(12) United States Patent
Seto et al.

(10) Patent No.: US 9,752,143 B2
(45) Date of Patent: Sep. 5, 2017

(54) LOCKED NUCLEIC ACID INHIBITOR OF MIR-145 AND USES THEREOF

(71) Applicant: MIRAGEN THERAPEUTICS, INC., Boulder, CO (US)

(72) Inventors: Anita G. Seto, Golden, CO (US); Eva van Rooij, Utretcht (NL); Kathryn H. Hutnick, Boulder, CO (US); Christina M. Dalby, Boulder, CO (US); Thomas G. Hullinger, Boulder, CO (US); Rusty Montgomery, Boulder, CO (US)

(73) Assignee: MIRAGEN THERAPEUTICS, INC., Boulder, CO (US)

( * ) Notice: Subject to any disclaimer, the term of this patent is extended or adjusted under 35 U.S.C. 154(b) by 0 days.

(21) Appl. No.: 14/777,172

(22) PCT Filed: Mar. 13, 2014

(86) PCT No.: PCT/US2014/026538
§ 371 (c)(1),
(2) Date: Sep. 15, 2015

(87) PCT Pub. No.: WO2014/151835
PCT Pub. Date: Sep. 25, 2014

(65) Prior Publication Data
US 2016/0010091 A1    Jan. 14, 2016

Related U.S. Application Data

(60) Provisional application No. 61/800,755, filed on Mar. 15, 2013.

(51) Int. Cl.
| | | |
|---|---|---|
| C07H 21/04 | (2006.01) | |
| C12N 15/113 | (2010.01) | |
| A61K 31/713 | (2006.01) | |
| C07H 21/00 | (2006.01) | |

(52) U.S. Cl.
CPC .......... *C12N 15/113* (2013.01); *A61K 31/713* (2013.01); *C07H 21/00* (2013.01); *C12N 2310/113* (2013.01); *C12N 2310/315* (2013.01); *C12N 2310/321* (2013.01); *C12N 2310/322* (2013.01); *C12N 2310/3231* (2013.01)

(58) Field of Classification Search
CPC ..................................................... C07H 21/04
See application file for complete search history.

(56) References Cited

U.S. PATENT DOCUMENTS

| | | | |
|---|---|---|---|
| 8,431,542 | B2 | 4/2013 | Wang et al. |
| 9,072,764 | B2 | 7/2015 | Wang et al. |
| 9,267,134 | B2 | 2/2016 | Baker et al. |
| 2004/0157790 | A1 | 8/2004 | Herweijer et al. |
| 2004/0242528 | A1 | 12/2004 | Hagstrom et al. |
| 2005/0059005 | A1 | 3/2005 | Tuschl et al. |
| 2005/0124566 | A1 | 6/2005 | Robin et al. |
| 2005/0261218 | A1 | 11/2005 | Esau et al. |
| 2006/0246491 | A1 | 11/2006 | Srivastava |
| 2006/0247193 | A1 | 11/2006 | Taira et al. |
| 2009/0176723 | A1 | 7/2009 | Brown et al. |
| 2010/0004320 | A1 | 1/2010 | Elmen et al. |
| 2010/0292297 | A1 | 11/2010 | Wang et al. |
| 2010/0298222 | A1 | 11/2010 | Dewhirst et al. |
| 2010/0298410 | A1 | 11/2010 | Obad et al. |
| 2012/0148664 | A1 | 6/2012 | Dalby et al. |
| 2013/0225658 | A1 | 8/2013 | Wang et al. |
| 2013/0225665 | A1 | 8/2013 | Wang et al. |
| 2014/0163086 | A1 | 6/2014 | Baker et al. |

FOREIGN PATENT DOCUMENTS

| | | |
|---|---|---|
| CN | 102382824 A | 3/2012 |
| WO | WO 2004/076622 A2 | 9/2004 |
| WO | WO 2006/107826 A2 | 10/2006 |
| WO | WO 2007/070483 A2 | 6/2007 |
| WO | WO 2007/122754 A2 | 10/2007 |
| WO | WO 2009/121031 A1 | 10/2009 |
| WO | WO 2010/104796 A2 | 9/2010 |
| WO | WO 2010/144485 A1 | 12/2010 |
| WO | WO 2012/083005 A2 | 6/2012 |
| WO | WO 2012/153135 A1 | 11/2012 |
| WO | WO 2013/192576 A2 | 12/2013 |

OTHER PUBLICATIONS

Ambros, "The functions of animal microRNAs," Nature, vol. 431, pp. 350-355 (2004).
Bartel, "MicroRNAs: genomics, biogenesis, mechanism, and function," Cell, vol. 116, pp. 281-297 (2004).
Basyuk et al., "Human let-7 stem-loop precursors harbor features of RNase III cleavage products,"Nucleic Acids Res. vol. 31, pp. 6593-6597 (2003).
Batkai and Thum, "MicroRNAs in Hypertension: Mechanisms and Therapeutic Targets," Curr Hypertens. Rep. 14:79-87 (2012).
Bernstein et al., "Dicer is essential for mouse development," Nat. Genet., vol. 35, pp. 215-217 (2003).
Blau et al., "Plasticity of the differentiated state," Science, vol. 230, pp. 758-766 (1985).
Bockmeyer et al., "Expression of Mir143/145 and Smooth Muscle Differentiation Markers in Vascular Compartments of Pulmonary Hypertension," Am. J. Respir. Crit. Care Med. 183(1): Supp. Meeting Abstracts, No. A3447 (2011).
Boettger et al., "Acquisition of the contractile phenotype by murine arterial smooth cells depends on the Mir143/145 gene cluster," J. Clin. Invest. 119(9):2634-2647 (2009).

(Continued)

*Primary Examiner* — Kimberly Chong
(74) *Attorney, Agent, or Firm* — Cooley LLP

(57) ABSTRACT

The present invention provides oligonucleotides with chemical motifs that are miR-145 inhibitors. The oligonucleotides can be used for the treatment and prevention of a condition by inhibiting the expression or activity of miR-145 in cells of a subject in need thereof. Methods provided include treating or preventing pulmonary arterial hypertension, neointima formation, restenosis or hypertension in a subject in need thereof by administering to the subject an inhibitor of miR-145 expression or activity. Pharmaceutical compositions and kits comprising miR-145 inhibitors are also disclosed.

19 Claims, 10 Drawing Sheets

(56) References Cited

OTHER PUBLICATIONS

Bohnsack et al., "Exportin 5 is a RanGTP-dependent dsRNA-binding protein that mediates nuclear export of pre-miRNAs," RNA, vol. 10, pp. 185-191 (2004).
Bonin et al., "The eyes absent gene: genetic control of cell survival and differentiation in the developing *Drosophila* eye," Cell, vol. 72, pp. 379-395 (1993).
Borsani et al., "EYA4, a novel vertebrate gene related to *Drosophila* eyes absent," Hum. Mol. Genet., vol. 8, pp. 11-23 (1999).
Bracht et al., "Trans-splicing and polyadenylation of let-7 microRNA primary transcripts," RNA, vol. 10, pp. 1586-1594. (2004).
Brown et al., "Tbx5 and Tbx20 act synergistically to control vertebrate heart morphogenesis," Development, vol. 132, pp. 553-563 (2005).
Cao et al., "Modulation of smooth muscle gene expression by association of histone acetyltransferases and deacetylases with myocardia," Mol. Cell Biol., vol. 25, pp. 364-376 (2005).
Caruso et al., "Dynamic Changes in Lung MicroRNA Profiles During the Development of Pulmonary Hypertension due to Chronic Hypoxia and Monocrotaline," Arterioscler. Thromb. Vasc. Biol. 30(4):716-723 (2010).
Caruso et al., "A Role for miR-145 in Pulmonary Arterial Hypertension. Evidence From Mouse Models and Patient Samples," Circ. Res. 111(3):290-300 (2012).
Chang et al., "MicroRNAs act sequentially and asymmetrically to control chemosensory laterality in the nematode," Nature, vol. 430, pp. 785-789 (2004).
Chen et al., "MicroRNAs modulate hematopoietic lineage differentiation," Science, vol. 303, pp. 83-86 (2004).
Chen et al., "The Role of Microrna-1 and Microrna-133 in Skeletal Muscle Proliferation and Differentiation," Nature Genetics, vol. 38, No. 2, pp. 228-233 (Feb. 1, 2006).
Chen et al., "microRNAs and muscle disorders," J. Cell Sci. 122:13-20 (2009).
Communication pursuant to Article 94(3) EPC corresponding to European Patent Application No. 06 845 222.6-1212 dated Jul. 12, 2011.
Conlon et al "Inhibition of Xbra transcription activation causes defects in mesodermal patterning and reveals autoregulation of Xbra in dorsal mesoderm," Development, vol. 122, pp. 2427-2435 (1996).
Cordes et al., "miR-145 and miR-143 regulate smooth muscle cell fate and plasticity," Nature 460:705-711 (2009).
Cotta-de-Almeida et al., "A new method for rapidly generating gene targeting vectors by engineering BACs through homologous recombination in bacteria," Genome Res., vol. 13, 2190-2194 (2003).
Courboulin et al., "Role for miR-204 in human pulmonary arterial hypertension," J. Exp. Med. 208(3):535-548 (2011).
Czubryt et al., "Regulation of peroxisome proliferator-activated receptor gamma coactivator 1 alpha (PGC-1 alpha) and mitochondrial' function by MEF2 and HDAC5," Proc. Natl. Acad. Sci. USA, vol. 100, pp. 1711-1716 (2003).
Darling et al., "Different dimerization activities of alpha and beta thyroid hormone receptor isoforms," J. Biol. Chem., vol. 268, 10221-10227 (1993).
Doench and Sharp, "Specificity of microRNA target selection in translational repression," Genes Dev., vol. 18, pp. 504-511 (2004).
Ebel et al. (1992). Very stable mismatch duplexes: structural and thermodynamic studies on tandem G.A mismatches in DNA. Biochem 31:12083-12086.
Elia et al., "The knockout of miR-143 and -145 alters smooth muscle cell maintenance and vascular homeostasis in mice: correlates with human disease," Cell Death and Differentiation 16:1590-1598 (2009).
Esau et al., "MicroRNA-143 regulates adipocyte differentiation," J. Biol. Chem., vol. 279, pp.52361-52365 (2004).
European Search Report Corresponding to European Patent Application No. 13177425.9-1401 dated Nov. 11, 2013.
Everett et al. "Regulation of myosin synthesis by thyroid hormone: relative change in the alpha- and beta-myosin heavy chain mRNA levels in rabbit heart," Biochemistry, vol. 23, pp. 1596-1599 (1984).
European Search Report corresponding to European Patent Application No. 12166173.0-1212 dated Aug. 14, 2012.
Fondell et al., "Ligand induction of a transcriptionally active thyroid hormone receptor coactivator complex," Proc. Natl. Acad. Sci. USA, vol. 93, pp. 8329-8333 (1996).
Freier et al., "Improved free-energy parameters for predictions of RNA duplex stability," Proc. Natl. Acad. Sci. USA, vol. 83, pp. 9373-9377 (1986).
Giraldez et al., "MicroRNAs regulate brain morphogenesis in zebrafish," Science, vol. 308, pp. 833-838 (2005).
Granzier and Labeit, "The giant protein titin: a major player in myocardial mechanics, signaling, and disease," Circ. Res., vol. 94, 284-295 (2004).
Griffiths-Jones, S., "The microRNA Registry," NAR, vol. 32, Database Issue, pp. D109-D111 (2004).
Grishok et al., "Genes and mechanisms related to RNA interference regulate expression of the small temporal RNAs that control C. elegans developmental timing," Cell, vol. 106, pp. 23-34 (2001).
Gustafson et al., "Thyroid hormone regulates expression of a transfected alpha-myosin heavy-chain fusion gene in fetal heart cells," Proc. Natl. Acad. Sci. USA, vol. 84, pp. 3122-3126 (1987).
Gwizdek et al., "Minihelix-containing RNAs mediate exportin-5-dependent nuclear export of the double-stranded RNA-binding protein IIF3," J. Biol. Chem., vol. 279, pp. 884-891 (2004).
Hagen et al., "Cloning by recognition site screening of two novel GT box binding proteins: a family of Sp1 related genes," Nucleic Acids Res., vol. 20, pp. 5519-5525 (1992).
Hagen et al., "Sp1-mediated transcriptional activation is repressed by Sp3," Embo. J., vol. 13, 3843-3851 (1994).
Harfe et al., "The RNaseIII enzyme Dicer is required for morphogenesis but not patterning of the vertebrate limb," Proc. Nat'l Acad. Sci. U S A., 102: 10898-10903 (2005).
He et al., "A microRNA polycistron as a potential human oncogene," Nature, vol. 435, pp. 828-833.
Heanue et al., "Synergistic regulation of vertebrate muscle development by Dach2, Eya2, and Six1, homologs of genes required for *Drosophila* eye formation," Genes Dev., vol. 13, pp. 3231-3243 (1999).
Henikoff & Henikoff, "Amino acid substitution matrices from protein blocks," Proc. Natl. Acad. Sci. USA, vol. 89, pp. 10915-10919 (1992).
Hutvagner et al., "A cellular function for the RNA-interference enzyme Dicer in the maturation of the let-7 small temporal RNA," Science, vol. 293, pp. 834-838 (2001).
Hutvagner et al., "Sequence-specific inhibition of small RNA function," PLoS Biol., vol. 2, E98 (2004).
International Preliminary Report on Patentability, Chapter 1 of the Patent Cooperation Treaty, for international application No. PCT/US2006/047255, dated Jun. 18, 2008.
International Search Report corresponding to International Application No. PCT/US2006/047255 dated May 22, 2008.
International Search Report, PCT Appl. No. PCT/GB2012/051018, 5 pages (Oct. 25, 2012).
International Search Report, PCT appl. No. PCT/US2014/026538, 4 pages (mailed Jul. 10, 2014).
Iorio et al., "MicroRNA gene 1-17 expression deregulation in human breast cancer," Cancer Research, vol. 65, No. 16, pp. 7065-7070 (Aug. 15, 2005).
Ito et al., "Identity between TRAP and SMCC complexes indicates novel pathways for the function of nuclear receptors and diverse mammalian activators," Mol. Cell., vol. 3, pp. 361-370 (1999).
Ito et al., "Involvement of the TRAP220 component of the TRAP/SMCC coactivator complex in embryonic development and thyroid hormone action," Mol. Cell., vol. 5, pp. 683-693 (2000).
James et al., "Molecular remodeling of cardiac contractile function," Am. J. Physiol., vol. 273, H2105-H2118 (1997).
John et al., "Human MicroRNA targets," PLoS Biol 2, e363 (2004).
Johnston et al., "A microRNA controlling left/right neuronal asymmetry in Caenorhabditis elegans," Nature, vol. 426, pp. 845-849 (2003).

(56) References Cited

OTHER PUBLICATIONS

Jones et al., "Ablation of the murine alpha myosin heavy chain gene leads to dosage effects and functional deficits in the heart," J. Clin. Invest., vol. 98, pp. 1906-1917 (1996).
Joshi et al., "Mir-145 in Vascular Smooth Muscle Phenotype in Pulmonary Arterial Hypertension," Am. J. Respir. Crit. Care Med. 183(1): Supp. Meeting Abstracts, No. A3447 (2011).
Karlin & Altschul, "Applications and statistics for multiple high-scoring segments in molecular sequences," Proc. Natl. Acad. Sci. USA, vol. 90, pp. 5873-5877 (1993).
Ketting et al., "Dicer functions in RNA interference and in synthesis of small RNA involved in developmental timing in C. elegans," Genes Dev., vol. 15, pp. 2654-2659 (2001).
Khvorova et al., "Functional siRNAs and miRNAs exhibit strand bias," Cell, vol. 115, pp. 209-216 (2003).
Kim et al., "MicroRNA miR-206 promotes muscle differentiation," The Journal of Cell Biology, vol. 174, No. 5, pp. 677-687 (Aug. 21, 2006).
Kiriakidou et al., "A combined computational-experimental approach predicts human microRNA.targets," Genes Dev., vol. 18, pp. 1165-1178 (2004).
Krek et al., "Combinatorial microRNA target predictions," Nat. Genet., vol. 37, pp. 495-500 (2005).
Kroll et al., "Transgenic Xenopus embryos from sperm nuclear transplantations reveal FGF signaling requirements during gastrulation," Development, vol. 122, pp. 3173-3183. (1996).
Lagos-Quintana et al., "Identification of tissue-specific microRNAs from mouse," Curr. Biol., vol. 12, No. 9, pp. 735-739 (Apr. 30, 2002).
Lagos-Quintana et al.,"New microRNAs from mouse and human," RNA, vol. 9, No. 2, pp. 175-179 (Feb. 2003).
Lee et al., "An extensive class of small RNAs in Caenorhabditis elegans," Science, vol. 294, pp. 862- 864 (2001).
Lee et al., "MicroRNA genes are transcribed by RNA polymerase II," Embo. J., vol. 23, pp. 4051-4060 (2004).
Lee et al., "The C. elegans heterochronic gene lin-4 encodes small RNAs with antisense complementarity to lin-14," Cell, vol. 75, pp. 843-854 (1993).
Lee et al., "The nuclear RNase III Drosha initiates microRNA processing," Nature, vol. 425, pp. 415-419 (2003).
Lewis et al., "Prediction of mammalian microRNA targets," Cell, vol. 115, pp. 787-798 (2003).
Li et al., "Requirement for serum response factor for skeletal muscle growth and maturation revealed by tissue-specific gene deletion in mice," Proc. Nat'l Acad. Sci. USA, vol. 102, pp. 1082-1087 (2005).
Liu et al., "A highly efficient recombineering-based method for generating conditional knockout mutations," Genome Res. vol. 13, pp. 476-484 (2003).
Lompre et al., "Expression of the cardiac ventricular alpha- and beta-myosin heavy chain genes is developmentally and hormonally regulated," J. Biol. Chem., vol. 259, pp. 6437-6446 (1984).
Lu et al., "Regulation of skeletal myogenesis by association of the MEF2 transcription factor with class II histone deacetylases," Mol. Cell, vol. 6 pp. 233-244 (2000).
Lund et al., "Nuclear export of microRNA precursors," Science, vol. 303, pp. 95-98 (2004).
Mansfield et al., "MicroRNA-responsive 'sensor' transgenes uncover Hox-like and other developmentally regulated patterns of vertebrate microRNA expression," Nat. Genet., vol. 36, pp. 1079-1083 (2004).
McCroskery et al., "Improved muscle healing through enhanced regeneration and reduced fibrosis in myostatin-null mice," Journal of Cell Science, vol. 118, pp. 3531-3541 (Jan. 1, 2005).
McKinsey et al., "Signal-dependent nuclear export of a histone deacetylase regulates muscle differentiation," Nature, vol. 408, pp. 106-111 (2000).
Meister et al., "Sequence-specific inhibition of microRNA- and siRNA-induced RNA silencing.," RNA, vol. 10, pp. 544-550 (2004).

Muncke et al., "Missense mutations and gene interruption in PROSIT240, a novel TRAP240-like gene, in patients with congenital heart defect (transposition of the great arteries)," Circulation, vol. 108, pp. 2843-2850 (2003).
Needleman & Wunsch, "A general method applicable to the search for similarities in the amino acid sequence of two proteins," J Mol Biol. 48:443-453 (1970).
Nicol et al., "Activated MEK5 induces serial assembly of sarcomeres and eccentric cardiac hypertrophy," Embo. J., vol. 20, pp. 2757-2767 (2001).
Pearson & Lipman, "Improved tools for biological sequence comparison," Proc. Natl. Acad. Sci. USA, vol. 85, pp. 2444-2448 (1988).
Pillai et al., "Tethering of human go proteins to mRNA mimics the miRNA-mediated repression of protein synthesis," RNA, vol. 10, 1518-1525 (2004).
Pinna et al., "Protein kinase CK2 (casein kinase-2) and its implication in cell division and proliferation," Prog. Cell Cycle Res., vol. 3, pp. 77-97 (1997).
Poy et al., "A pancreatic islet-specific microRNA regulates insulin secretion," Nature, vol. 432, pp. 226-230 (2004).
Rajewsky et al., "Computational identification of microRNA targets," Dev. Biol., vol. 267, pp. 529-535 (2004).
Rodriguez et al., "Identification of mammalian microRNA host genes and transcription units," Genome Res., vol. 14, pp. 1902-1910 (2004).
Sanbe et al., Reengineering inducible cardiac-specific transgenesis with an attenuated myosin heavy chain promoter. Circ. Res., vol. 92, pp. 609-616 (2003).
Santalucia et al., "Factors involved in GLUT-1 glucose transporter gene transcription in cardiac muscle," J. Biol. Chem., vol. 274, pp. 17626-17634 (1999).
Schonberger et al., "Mutation in the transcriptional coactivator EYA4 causes dilated cardiomyopathy and sensorineural hearing loss," Nat. Genet., vol. 37, pp. 418-422 (2005).
Schwarz et al., "Asymmetry in the assembly of the RNAi enzyme complex," Cell, vol. 115, pp. 199-208 (2003).
Sempere et al., "Expression profiling of mammalian microRNAs uncovers a subset of brain-expressed microRNAs with possible roles in murine and human neuronal differentiation," Genome Biol., vol. 5, R13 (2004).
Sokol et al., "Mesodermally expressed *Drosophila* microRNA-1 is regulated by Twist and is required in muscles during larval growth" Genes and Development, vol. 19, No. 19, pp. 2343-2354 (Oct. 1, 2005).
Soulez et al., "Growth and differentiation of C2 myogenic cells are dependent on serum response factor," Mol. Cell Biol., vol. 16, pp. 6065-6074 (1996).
Subramaniam et al., "Tissue-specific regulation of the alpha-myosin heavy chain gene promoter in transgenic mice," J. Biol. Chem., vol. 266, pp. 24613-24620 (1991).
Subramaniam et al., "Transgenic analysis of the thyroid-responsive elements in the alpha-cardiac myosin heavy chain gene promoter," J. Biol. Chem., vol. 268, 4331-4336 (1993).
Supplementary European Search Report corresponding to European Patent Application No. 06 845 222.6 dated Sep. 17, 2010.
Supplementary European Search Report, EP appl. No. 14768310.6, 7 pages (mailed Jul. 18, 2016).
Sweetman et al., "Specific requirements of MRFs for the expression of muscle specific microRNAs, miR-1, miR-206 and miR-133," Developmental Biology, vol. 321, No. 2, pp. 491-499 (Sep. 15, 2008).
Thomson et al., "A custom microarray platform for analysis of microRNA gene expression," Nat. Methods, vol. 1, pp. 47-53 (2004).
Tibanyenda et al., "The effect of single base-pair mismatches on the duplex stability of d(T-A-T-T-A-A-T-A-T-C-A-A-G-T-T-G). d(C-A-A-C-T-T-G-A-T-A-T-T-A-A-T-A)," Eur. J. Biochem., vol. 139, vol. 19-27 (1984).
Townley-Tilson et al., "MicroRNAs 1, 133, and 206: Critical factors of skeletal and cardiac muscle development, function, and disease," International Journal of Biochemistry and Cell Biology, vol. 42, No. 8, pp. 1252-1255 (Aug. 1, 2010).

(56) References Cited

OTHER PUBLICATIONS

Treisman, J., "*Drosophila* homologues of the transcriptional coactivation complex subunits TRAP240 and TRAP230 are required for identical processes in eye-antennal disc development," Development, vol. 128, pp. 603-615 (2001).
Turner et al., "Improved Parameters for Prediction of RNA Structure," Cold Spring Harb. Symp. Quant. Biol., LII, pp. 123-133 (1987).
Wang et al., "Activation of cardiac gene expression by myocardin, a transcriptional cofactor for serum response factor," Cell, vol. 105, 851-862 (2001).
Wang et al., "Regulation of cardiac growth and development by SRF and its cofactors," Cold Spring Harb. Symp Quant. Biol., vol. 67, pp. 97-105 (2002).
Wayne et al., "Mutations in the transcriptional activator EYA4 cause late-onset deafness at the DFNA10 locus," Hum. Mol. Genet., vol. 10, pp. 195-200 (2001).
Wienholds et al., "MicroRNA expression in zebrafish embryonic development," Science, vol. 309, pp. 310-311 (2005).
Wightman et al., "Posttranscriptional regulation of the heterochronic gene lin-14 by lin-4 mediates temporal pattern formation in C. elegans," Cell, vol. 75, pp. 855-862 (Dec. 3, 1993).
Written Opinion of the International Searching Authority, PCT Appl. No. PCT/GB2012/051018, 7 pages (Oct. 25, 2012).
Written Opinion of the International Searching Authority, PCT appl. No. PCT/US2014/026538, 5 pages (mailed Jul. 10, 2014).
Xu et al., "Murine protein kinase CK2α': cDNA and genomic cloning and chromosomal mapping," Genomics, vol. 48, pp. 79-86 (1998).
Yan et al., "Highly Coordinated Gene Regulation in Mouse Skeletal Muscle Regeneration," J. Biol. Chem., vol. 278, Issue 10, pp. 8826-8836 (2003).
Yekta et al., "MicroRNA-directed cleavage of HOXB8 mRNA," Science, vol. 304, pp. 594-596 (2004).
Yi et al., "Exportin-5 mediates the nuclear, export of pre-microRNAs and short hairpin RNAs," Genes Dev., vol. 17, pp. 3011-3016 (2003).
Yi et al., "Overexpression of exportin 5 enhances RNA interference mediated by short hairpin RNAs and microRNAs," RNA, vol. 11, pp. 220-226 (2005).
Zhao et al., "Regulation of MEF2 by Histone Deacetylase 4- and SIRT1 Deacetylase-Mediated Lysine Modifications," Mol. Cell. Biol. vol. 25, No. 19, pp. 8456-8464 (Oct. 2005).
Zhao et al., "Serum response factor regulates a muscle-specific microRNA that targets Hand2 during cardiogenesis," Nature, vol. 436, pp. 214-220 (2005).
Davis et al., "Improved targeting of miRNA with antisense oligonucleotides," Nucl. Acids Res. 34:2294-2304 (2006).

$ = p value of <0.05 from 10591

* compared to saline
^ compared to 10591

* compared to saline
^ compared to 10591

FIGURE 6A

| | | | | | BP/<br>Terminal<br>PWV |
|---|---|---|---|---|---|
| | | | | L-NAME | ↓ |
| Age of SHR<br>(weeks) | 16 | 17 | 18 | 19 | 20 |
| | ↑ | ↑ | ↑ | ↑ | |
| | | antimiR dosing (25 mg/kg) | | | |

SEQUENCE LISTING

<160> NUMBER OF SEQ ID NOS: 20

<210> SEQ ID NO 1
<211> LENGTH: 23
<212> TYPE: RNA
<213> ORGANISM: Homo sapiens

<400> SEQUENCE: 1
guccaguuuu cccaggaauc ccu            23

```
<210> SEQ ID NO 2
<211> LENGTH: 22
<212> TYPE: RNA
<213> ORGANISM: Homo sapiens

<400> SEQUENCE: 2
ggauuccugg aaauacuguu cu                                              22

<210> SEQ ID NO 3
<211> LENGTH: 88
<212> TYPE: RNA
<213> ORGANISM: Homo sapiens

<400> SEQUENCE: 3
caccuugucc ucacggucca guuucccag gaaucccuua gaugcuaaga uggggauucc      60
uggaaauacu guucuugagg ucaugguu                                        88

<210> SEQ ID NO 4
<211> LENGTH: 23
<212> TYPE: RNA
<213> ORGANISM: Mus sp.

<400> SEQUENCE: 4
guccaguuuu cccaggaauc ccu                                             23

<210> SEQ ID NO 5
<211> LENGTH: 22
<212> TYPE: RNA
<213> ORGANISM: Mus sp.

<400> SEQUENCE: 5
auuccuggaa auacuguucu ug                                              22

<210> SEQ ID NO 6
<211> LENGTH: 70
<212> TYPE: RNA
<213> ORGANISM: Mus sp.

<400> SEQUENCE: 6
cucacggucc aguuucccca ggaaucccuu ggaugcuaag auggggauuc cuggaaauac     60
uguucuugag                                                            70

<210> SEQ ID NO 7
<211> LENGTH: 8
<212> TYPE: RNA
<213> ORGANISM: Homo sapiens

<400> SEQUENCE: 7 uccaguuu                                                              8

<210> SEQ ID NO 8
<211> LENGTH: 22
<212> TYPE: RNA
<213> ORGANISM: Homo sapiens

<400> SEQUENCE: 8
uucccuuugu cauccuaugc cu                                              22

<210> SEQ ID NO 9
<211> LENGTH: 21
<212> TYPE: RNA
```

```
<213> ORGANISM: Homo sapiens

<400> SEQUENCE: 9
gcugggaagg caaagggacg u                                              21

<210> SEQ ID NO 10
<211> LENGTH: 23
<212> TYPE: DNA
<213> ORGANISM: Artificial Sequence
<220> FEATURE:
<223> OTHER INFORMATION: miR-145 RNA/DNA sequence

<400> SEQUENCE: 10
guccaguuuu cccaggaatc ccu                                            23

<210> SEQ ID NO 11
<211> LENGTH: 23
<212> TYPE: DNA
<213> ORGANISM: Artificial Sequence
<220> FEATURE:
<223> OTHER INFORMATION: miR-145 reverse complement

<400> SEQUENCE: 11
agggattcct gggaaaactg gac                                            23

<210> SEQ ID NO 12
<211> LENGTH: 16
<212> TYPE: DNA
<213> ORGANISM: Artificial Sequence
<220> FEATURE:
<223> OTHER INFORMATION: antimiR 10934
<220> FEATURE:
<221> NAME/KEY: MOD_RES
<222> LOCATION: (1)..(16)
<223> OTHER INFORMATION: May be a locked nucleic acid residue

<400> SEQUENCE: 12
tcctgggaaa actgga                                                    16

<210> SEQ ID NO 13
<211> LENGTH: 16
<212> TYPE: DNA
<213> ORGANISM: Artificial Sequence
<220> FEATURE:
<223> OTHER INFORMATION: antimiR 11239
<220> FEATURE:
<221> NAME/KEY: MOD_RES
<222> LOCATION: (1)..(16)
<223> OTHER INFORMATION: May be a locked nucleic acid residue

<400> SEQUENCE: 13
tcctgggaaa actgga                                                    16

<210> SEQ ID NO 14
<211> LENGTH: 16
<212> TYPE: DNA
<213> ORGANISM: Artificial Sequence
<220> FEATURE:
<223> OTHER INFORMATION: antimiR 11241
<220> FEATURE:
<221> NAME/KEY: MOD_RES
<222> LOCATION: (1)..(16)
<223> OTHER INFORMATION: May be a locked nucleic acid residue

<400> SEQUENCE: 14
tcctgggaaa actgga                                                    16
```

-continued

```
<210> SEQ ID NO 15
<211> LENGTH: 16
<212> TYPE: DNA
<213> ORGANISM: Artificial Sequence
<220> FEATURE:
<223> OTHER INFORMATION: antimiR 11242
<220> FEATURE:
<221> NAME/KEY: MOD_RES
<222> LOCATION: (1)..(16)
<223> OTHER INFORMATION: May be a locked nucleic acid residue

<400> SEQUENCE: 15
tcctgggaaa actgga                                                        16

<210> SEQ ID NO 16
<211> LENGTH: 16
<212> TYPE: DNA
<213> ORGANISM: Artificial Sequence
<220> FEATURE:
<223> OTHER INFORMATION: antimiR 11244
<220> FEATURE:
<221> NAME/KEY: MOD_RES
<222> LOCATION: (1)..(16)
<223> OTHER INFORMATION: May be a locked nucleic acid residue

<400> SEQUENCE: 16
tcctgggaaa actgga                                                        16

<210> SEQ ID NO 17
<211> LENGTH: 16
<212> TYPE: DNA
<213> ORGANISM: Artificial Sequence
<220> FEATURE:
<223> OTHER INFORMATION: antimiR 11318
<220> FEATURE:
<221> NAME/KEY: MOD_RES
<222> LOCATION: (1)..(16)
<223> OTHER INFORMATION: May be a locked nucleic acid residue

<400> SEQUENCE: 17
tcctgggaaa actgga                                                        16

<210> SEQ ID NO 18
<211> LENGTH: 16
<212> TYPE: DNA
<213> ORGANISM: Artificial Sequence
<220> FEATURE:
<223> OTHER INFORMATION: antimiR 11319
<220> FEATURE:
<221> NAME/KEY: MOD_RES
<222> LOCATION: (1)..(16)
<223> OTHER INFORMATION: May be a locked nucleic acid residue

<400> SEQUENCE: 18
tcctgggaaa actgga                                                        16

<210> SEQ ID NO 19
<211> LENGTH: 16
<212> TYPE: DNA
<213> ORGANISM: Artificial Sequence
<220> FEATURE:
<223> OTHER INFORMATION: antimiR 11320
<220> FEATURE:
<221> NAME/KEY: MOD_RES
<222> LOCATION: (1)..(16)
<223> OTHER INFORMATION: May be a locked nucleic acid residue

<400> SEQUENCE: 19
tcctgggaaa actgga                                                        16
```

```
<210> SEQ ID NO 20
<211> LENGTH: 16
<212> TYPE: DNA
<213> ORGANISM: Artificial Sequence
<220> FEATURE:
<223> OTHER INFORMATION: antimiR 11321
<220> FEATURE:
<221> NAME/KEY: MOD_RES
<222> LOCATION: (1)..(16)
<223> OTHER INFORMATION: May be a locked nucleic acid residue

<400> SEQUENCE: 20
tcctgggaaa actgga                                                 16
```

LOCKED NUCLEIC ACID INHIBITOR OF MIR-145 AND USES THEREOF

CROSS-REFERENCE

This application is a U.S. National Phase application, filed under 35 U.S.C. §371, of International Application No. PCT/US14/26538, filed on Mar. 13, 2014, which claims the benefit of U.S. provisional Application No. 61/800,755, filed on Mar. 15, 2013, the contents of each of which are herein incorporated by reference in their entireties.

DESCRIPTION OF THE TEXT FILE SUBMITTED ELECTRONICALLY

The contents of the text file submitted electronically herewith are incorporated herein by reference in their entirety: A computer readable format copy of the Sequence listing (filename: MIRG_041_01US_SeqList_ST25.txt, date recorded: Sep. 15, 2015, file size 5 kilobytes).

FIELD OF THE INVENTION

The present invention relates generally to oligonucleotides with chemical motifs that are miR-145 inhibitors. The oligonucleotides of the present invention can have advantages in potency, efficiency of delivery, target specificity, stability, and/or toxicity when administered to a subject. The oligonucleotides can be used for the treatment and prevention of a condition by inhibiting the expression or activity of miR-145 in cells of a subject in need thereof. Methods provided include treating or preventing pulmonary arterial hypertension, hypertension, neointima formation or restenosis in a subject in need thereof by administering to the subject an inhibitor of miR-145 expression or activity.

BACKGROUND OF THE INVENTION

MicroRNAs (miRNAs) are a class of small, endogenous and non-coding RNAs able to negatively regulate gene expression by targeting specific messenger RNAs (mRNAs) and inducing their degradation or translational repression (Ambros, 2004; Bartel, 2009). A recent study has defined mRNA degradation as the predominant mechanistic effect of miRNA:mRNA targets (Guo el al., 2010). Several recent studies have assessed the direct role of miRNAs in vascular inflammation and in the development of vascular pathologies (Kartha and Subramanian, 2010; Urbich et al., 2008).

MiR-145 was shown to be abundantly expressed in the vessel wall (Cheng et al., 2009). MiR-145 is transcribed as a long pri-miRNA encoding both miR-143 and miR-145 on human chromosome 5 (Lio et al., 2010) and on mouse chromosome 18, regulated by a conserved SRF-binding site (Xin et al., 2009). Localization of miR-145 to the vessel wall demonstrated high expression in the smooth muscle layer in comparison with adventitial fibroblasts and endothelial cells (Cheng et al., 2009). For this reason, miR-145 is considered a smooth muscle cell phenotypic marker and modulator, able to regulate smooth muscle cell (SMC) maturation and proliferation, and vascular neointimal lesion formation through its target gene KLF-5 and its downstream signaling molecule, myocardin (Cheng et al., 2009; Elia et al., 2009).

Agonists within the TGF-β superfamily have been shown to active miR-143/145 cluster via a Smad-dependent pathway (Davis-Dusenbery et al., 2011; Long et al., 2011). Moreover the analysis of miR-145, miR-143 and miR-143/145 knock-out (ko, –/–) mice showed a noticeably thinner smooth muscle layer of the aorta and other peripheral arteries, due to a reduced SMC size induced by a disruption of actin filaments (Elia et al., 2009). This leads to moderate systemic hypotension and the absence of neointima formation in response to injury in miR-145 –/– mice (Xin et al., 2009). Moreover, vascular smooth muscle cells (VSMCs) isolated from single and double ko animals showed hyperproliferative activity and a higher ability to migrate towards platelet-derived growth factor (PDGF), a known chemoattractant for VSMCs (Elia et al., 2009; Xin et al., 2009). Furthermore, a pharmacological analysis of the vasculature of miR-143(145) ko mice revealed a blunted response to vasopressive stimuli (Elia et al., 2009; Xin el al., 2009). Taking together, these findings show a dedifferentiated phenotype of VSMCs in miR-145 ko and miR-143/145 double ko mice.

Pre- and mature forms of miR-145 are also elevated in lung tissues and isolated pulmonary artery smooth muscle cells (PASMCs) obtained from pulmonary arterial hypertension (PAH) patients with a mutation in the BMPR2 gene compared to controls. One of the main histopathological features common to all forms of PAH is the accumulation of cells expressing smooth muscle specific α-actin (SMA) in peripheral pulmonary arteries. This includes the appearance of SMA-positive cells in the neointima and the extension of SMA-positive cells into precapillary pulmonary arterioles that are normally devoid of smooth muscle (Mandegar et al., 2004). The cellular processes responsible for the muscularization of this distal part of the PA are not clear, but these observations suggest a central role for PASMCs in the development of PAH.

Accordingly, miR-145, with a role in vascular remodeling, represents a therapeutic target the development of effective treatments for conditions associated with aberrant smooth muscle cell proliferation, such as in neointima formation, restensosis, hypertension, systemic hypertension and PAH. However, delivery of an antisense-based therapeutic targeting miR-145 can pose several challenges. The binding affinity and specificity to miR-145, efficiency of cellular uptake, and nuclease resistance are all factors in the delivery and activity of an oligonucleotide-based therapeutic. For example, when oligonucleotides are introduced into intact cells they are typically attacked and degraded by nucleases leading to a loss of activity. Thus, a useful antisense therapeutic should have good resistance to extra- and intracellular nucleases, as well as be able to penetrate the cell membrane.

Thus, there is a need for improved chemical modifications for stable and efficacious oligonucleotide-based inhibitors of miR-145. The present invention meets this need and provides related advantages as well.

SUMMARY OF THE INVENTION

The present invention is based, in part, on the discovery that an oligonucleotide targeting miR-145, such as an antisense to miR-145, with a specific chemical pattern or motif has increased potency, efficiency of delivery, target specificity, stability, and/or improved toxicity profile when administered to a subject. Specific chemistry patterns or motifs with the potential to improve the delivery, stability, potency, specificity, and/or toxicity profile of an antisense to miR-145, or an antimiR of miR-145 (i.e. antimiR-145) is provided herein. The chemistry patterns or motifs for an antisense to miR-145 can improve the delivery, stability, potency, specificity, and/or toxicity profile of an antimiR-145, thus, effectively targeting miR-145 function in a therapeutic context. Thus, the present invention provides a novel therapeutic for the treatment of a variety of diseases associated with miR-145 expression or activity, such as diseases or conditions associate with smooth muscle tissue.

Accordingly, the present invention provides an oligonucleotide comprising a sequence complementary to the seed region of miR-145, wherein the sequence comprises at least three locked nucleic acids (LNAs) and the oligonucleotide comprises at least one non-locked nucleotide. In some embodiments, the sequence of the oligonucleotide comprises at least four, five or six LNAs.

The oligonucleotide can have increased in vivo efficacy as compared to a second oligonucleotide comprising the same sequence and LNA composition and different LNA motif. In some embodiments, the oligonucleotide has increased lung efficacy as compared to the second oligonucleotide.

In some embodiments, the oligonucleotide increases the expression of a miR-145 target gene in a cell relative to a saline control, and the increase in expression has a p-value of <0.05. In some embodiments, the oligonucleotide increases the expression of a miR-145 target gene in a tissue relative to a saline control, and the increase in expression has a p-value of <0.05. In other embodiments, a cell treated with the oligonucleotide has a greater than 1.0 fold-change in the expression of a miR-145 target gene relative to a saline control, and the fold-change has a p-value of <0.05. In some embodiments, a tissue treated with the oligonucleotide has a greater than 1.0 fold-change in the expression of a miR-145 target gene relative to a saline control, and the fold-change has a p-value of <0.05. The fold-change in expression can be at least about 1.1, about 1.2, about 1.3, about 1.4, or about 1.5 fold. The miR-145 target gene can be Klf4, Klf5, Lrrc71, Nedd41, Igf1r, Sec1412, Megf6, Fmod, Ankrd12, Golga1, Gpbp1, Hist3h2a, Rapgef2, or Sned1.

The oligonucleotide can comprise a LNA at the 5' end, 3' end, or both the 5' and 3' ends. In some embodiments, the oligonucleotide comprises no more than three contiguous LNAs.

In some embodiments, the oligonucleotide comprises a 16-mer, wherein the 16-mer consists of sixteen nucleotides. The 16-mer can include the sequence complementary to the seed region of miR-145. In some embodiments, the 16-mer comprises at least nine LNAs. In some embodiments, the 16-mer, from 5' end to 3' end has LNAs at positions 1, 5, 6, 9, 10, 11, 13, 15, and 16; positions 1, 2, 6, 8, 10, 11, 13, 15, and 16; positions 1, 5, 6, 8, 10, 11, 13, 14, and 16; positions 1, 3, 4, 5, 6, 8, 10, 13, and 16; positions 1, 3, 4, 7, 8, 10, 12, 14, and 16; positions 1, 2, 6, 7, 10, 11, 12, 14, and 16; positions 1, 3, 5, 7, 9, 11, 13, 15, and 16; positions 1, 4, 5, 7, 9, 10, 12, 14, and 16; or positions 1, 5, 6, 8, 10, 11, 13, 15, and 16, of the 16-mer. The 16-mer can be substantially complementary to a nucleotide sequence of miR-145. In some embodiments, the 16-mer is completely complementary to miR-145.

The oligonucleotide can comprise at least one non-locked nucleotide that is 2' deoxy, 2' O-alkyl or 2' halo. In some embodiments, all of the non-locked nucleotides are 2' deoxy. The oligonucleotide can also comprise at least one LNA with a 2' to 4' methylene bridge. In some embodiments, the oligonucleotide has a 5' cap structure, 3' cap structure, or a 5' and 3' cap structure.

The oligonucleotide can also comprise one or more phosphorothioate linkages. In one embodiment, the oligonucleotide is fully phosphorothioate-linked. In yet other embodiments, the oligonucleotide has one to three phosphate linkages. In some embodiments, the oligonucleotide comprises a pendant lipophilic group. The oligonucleotide can be about 15 to 50 nucleotides in length.

Another aspect of the present invention is a pharmaceutical composition comprising an effective amount of an oligonucleotide described herein or a pharmaceutically-acceptable salt thereof, and a pharmaceutically-acceptable carrier or diluent. The pharmaceutically-acceptable carrier can comprise a colloidal dispersion system, macromolecular complex, nanocapsule, nanoparticle, microsphere, bead, oil-in-water emulsion, micelle, mixed micelle, or liposome. In some embodiments, the pharmaceutically-acceptable carrier or diluent consists essentially of saline.

In another aspect, the present invention provides methods for using an oligonucleotide disclosed herein. In one embodiment, a method for reducing or inhibiting activity of miR-145 in a cell comprising contacting the cell with an oligonucleotide disclosed herein is provided. In some embodiments, the cell is a smooth muscle cell. In yet other embodiments, the cell is a lung or cardiac cell. Also provided is a method for inhibiting smooth muscle cell proliferation comprising contacting a smooth muscle cell with an oligonucleotide disclosed herein. The cell can be a mammalian cell. The cell can be in vivo or ex vivo.

The present invention also provides a method for preventing or treating pulmonary arterial hypertension (PAH) in a subject comprising administering to the subject a pharmaceutical composition comprising an oligonucleotide disclosed herein. The PAH can be idiopathic pulmonary arterial hypertension (PAH), hereditary or familial PAH, or secondary pulmonary hypertension. The secondary pulmonary hypertension can be from pulmonary emboli, emphysema, pulmonary fibrosis, or congenital heart disease. The subject can have a mutation in the gene encoding the bone morphogenetic protein type-2 receptor. In some embodiments, the subject is diagnosed with or at risk of developing pulmonary hypertension or pulmonary arterial hypertension (PAH). The subject can be a mammal, such as a human.

The present invention also provides a method for inhibiting or treating restenosis or neointima formation in a subject comprising administering to the subject a pharmaceutical composition comprising an oligonucleotide disclosed herein. Also provided herein is a method for treating or preventing hypertension in a subject comprising administering to the subject a pharmaceutical composition comprising an oligonucleotide disclosed herein. In some embodiments, the hypertension is systemic hypertension. The subject can be a mammal, such as a human.

The pharmaceutical composition can be administered to the subject via various routes including, subcutaneously, intravenously, intraarterially, nasally, orally, or via a pulmonary route (e.g. via inhalation through the nose or mouth). In some embodiments, the pharmaceutical composition is administered by parenteral administration or by direct injection into cardiac tissue, such as for inhibiting, preventing or treating neointima formation or restenosis. In other embodiments, the pharmaceutical composition is administered by parenteral administration or by direct injection into lung tissue, such as for treating or preventing PAH. In one embodiment, the pharmaceutical composition is administered by an inhalational route through a pulmonary delivery device. In such embodiments, the pharmaceutical composition is formulated as a dry powder or liquid aerosol. In some embodiments, the pharmaceutical composition is administered by parenteral administration to treat or prevent hypertension.

Another aspect of the present invention is a kit comprising an oligonucleotide as described herein and an administration device. In one embodiment, the kit is for the treatment or prevention of pulmonary arterial hypertension. The administration device can be designed for pulmonary delivery, such as inhalers, nebulizers, insufflators, droppers, and aerosolizers. In other embodiments, the administration device can be designed for intravenous or intra-arterial delivery, such as a catheter. The pharmaceutical composition may be optionally formulated to be stored in the administration device. The kit may further comprise instructions for administering the pharmaceutical composition to a subject (e.g. human), such as for treating or preventing PAH, for inhibiting or treating restenosis or neointima formation, or treating or preventing hypertension.

DETAILED DESCRIPTION OF THE INVENTION

Figure 1A:
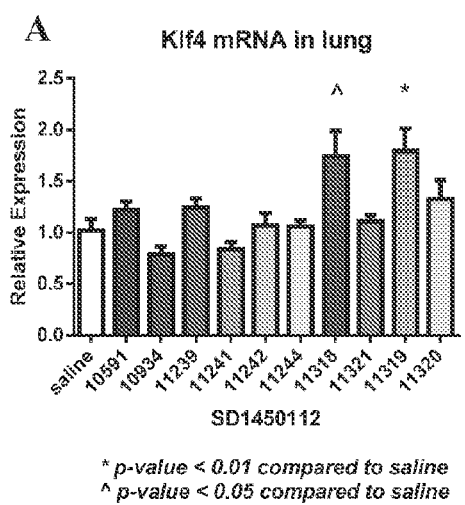
FIG. 1. Sprague-Dawley rats of 49 to 52 days of age were injected with a 25 mg/kg subcutaneous dose of an antimiR-145 compound from Table 1. Tissue was collected 48 hours after injection. The indicated mRNA levels of (A) Klf4, (B) Klf5, (C) Lrrc71, (D) Nedd41, (E) Igf1r, (F) Sec1412, (G) Megf6, (H) Fmod, (I) Ankrd12, (J) Golga1, (K) Gpbp1, (L) Hist3h2a, (M) Rapgef2, and (N) Sned1 were measured by real time PCR in total lung RNA. The results are shown as fold-change values relative to saline-treated animals.
Figure 1B:
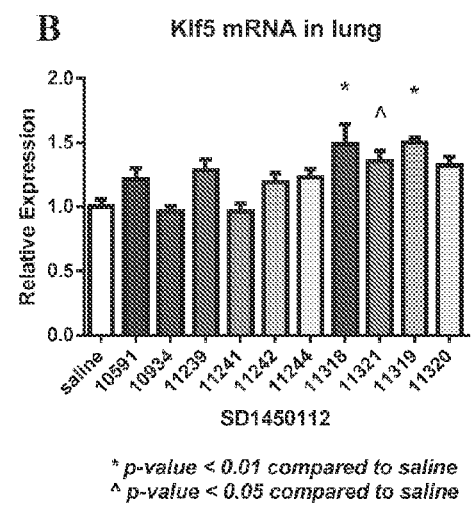
Figure 1C:
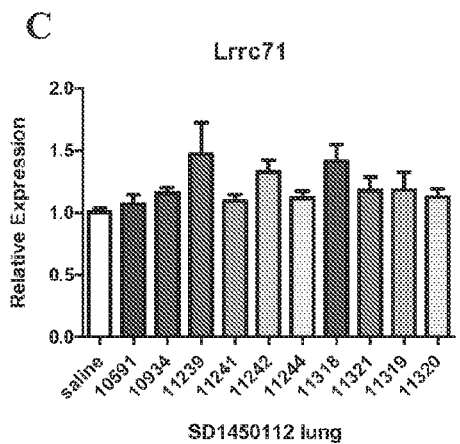
Figure 1D:
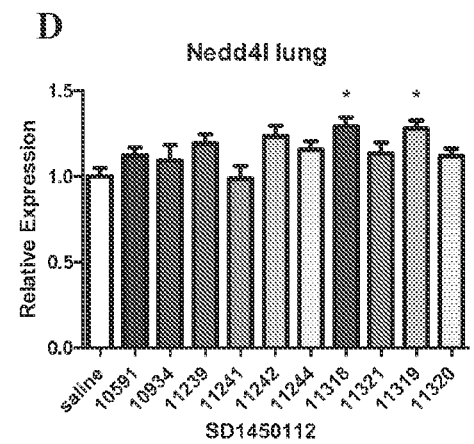
Figure 1E:
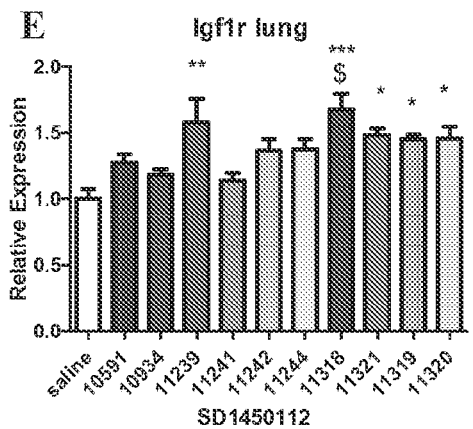
Figure 1F:
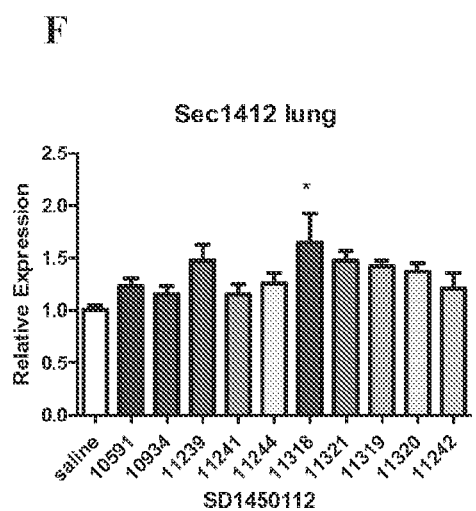
Figure 1G:
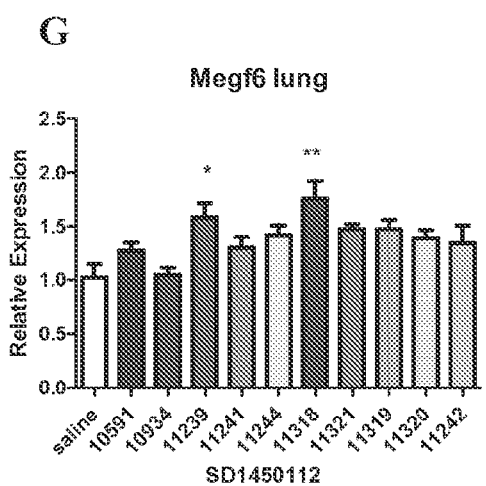
Figure 1H:
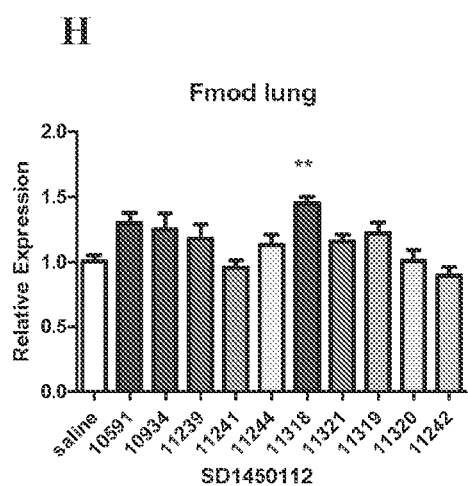
Figure 1I:
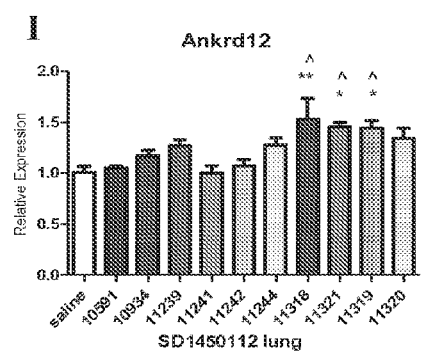
Figure 1J:
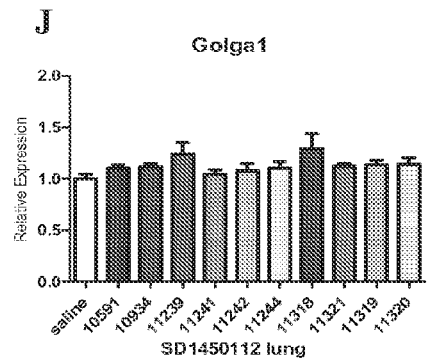
Figure 1K:
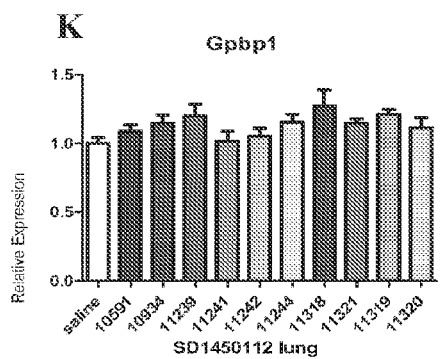
Figure 1L:
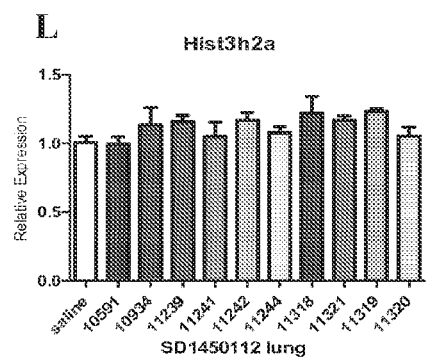
Figure 1M:
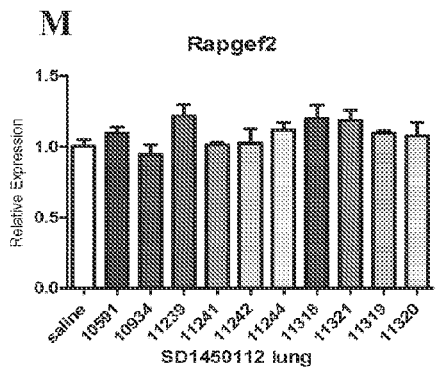
Figure 1N:
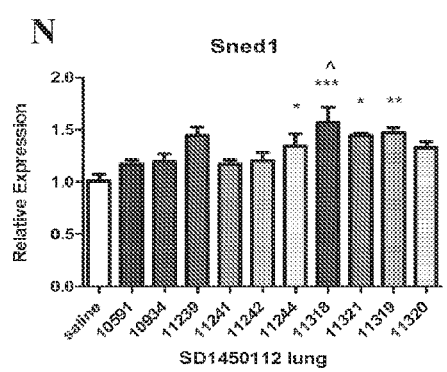

The present invention is based, in part, on the discovery that a specific chemical pattern or motif of an oligonucleotide targeting miR-145 can improve the potency, efficiency of delivery, target specificity, stability, and/or toxicity of the oligonucleotide when administered to a subject. In some embodiments, the oligonucleotide is capable of inhibiting, in a specific fashion, the expression or abundance of miR-145. The oligonucleotide with the specific chemical pattern or motif comprises a sequence complementary to miR-145, such as complementary to the seed region of miR-145. The oligonucleotide can be a miR-145 inhibitor, or antimiR-145.

MiR-145 is located in a cluster with miR-143 in an intergenic region on murine chromosome 18 and human chromosome 5. MiR-145 and miR-143, which have no homology to each other, are co-transcribed as a single transcript. The pre-miRNA sequence for miR-145 is processed into a mature sequence and a star (i.e. minor) sequence. The star sequence is processed from the other arm of the stem loop structure. The pre-miRNA (e.g. stem-loop sequences), mature, and star sequences for mouse and human miR-145 are given below:

```
Human mature miR-145
                                              (SEQ ID NO: 1)
5'-GUCCAGUUUUCCCAGGAAUCCCU-3'

Human miR-145*
                                              (SEQ ID NO: 2)
5'-GGAUUCCUGGAAAUACUGUUCU-3'

Human pre-miR-145
                                              (SEQ ID NO: 3)
5'-CACCUUGUCCUCACGGUCCAGUUUUCCCAGGAAUCCCUUAGAUGCUA
AGAUGGGGAUUCCUGGAAAUACUGUUCUUGAGGUCAUGGUU-3'

Mouse mature miR-145
                                              (SEQ ID NO: 4)
5'-GUCCAGUUUUCCCAGGAAUCCCU-3'

Mouse miR-145*
                                              (SEQ ID NO: 5)
5'-AUUCCUGGAAAUACUGUUCUUG-3'

Mouse pre-miR-145
                                              (SEQ ID NO: 6)
5'-CUCACGGUCCAGUUUUCCCAGGAAUCCCUUGGAUGCUAAGAUGGGGA
UUCCUGGAAAUACUGUUCUUGAG-3'
```

The above sequences can be either ribonucleic acid sequences or deoxyribonucleic acid sequences or a combination of the two (i.e. a nucleic acid comprising both ribonucleotides and deoxyribonucleotides). It is understood that a nucleic acid comprising any one of the sequences described herein will have a thymidine base in place of the uridine base for DNA sequences and a uridine base in place of a thymidine base for RNA sequences.

The oligonucleotide comprising a sequence complementary to miR-145, and with a particular chemical pattern or motif, can have increased in vivo efficacy as compared to an oligonucleotide with the same nucleotide sequence but different chemical pattern or motif. For example, a first and a second oligonucleotide each have the same nucleotide sequence that targets miR-145, including a sequence that is complementary to the seed region of miR-145. The first oligonucleotide has a chemical motif or pattern than differs from the second oligonucleotide. Both the first and second oligonucleotides are capable of reducing the expression or abundance of miR-145. However, the first oligonucleotide with a first chemical motif has higher in vive efficacy as compared to the second oligonucleotide with a different chemical motif, as measured by the amount of de-repression of a miR-145 target. The miR-145 target can be Klf4, Klf5, Lrrc71, Nedd41, Igf1r, Sec1412, Megf6, Fmod, Ankrd12, Golga1, Gpbp1, Hist3h2a, Rapgef2, or Sned1.

In some embodiments, the oligonucleotide increases the expression of a miR-145 target gene in a cell or tissue relative to a saline control, and the increase in expression has a p-value of <0.05. In some embodiments, the increase in expression has a p-value of <0.01. In other embodiments, a cell or tissue treated with the oligonucleotide has a greater than 1.0 fold-change in the expression of a miR-145 target gene relative to a saline control, and the fold-change has a p-value of <0.05. In some embodiments, the fold-change has a p-value of <0.01. The fold-change in expression can be at least about 1.1, about 1.2, about 1.3, about 1.4, or about 1.5 fold. The miR-145 target gene can be Klf4, Klf5, Lrrc71, Nedd41, Igf1r, Sec1412, Megf6, Fmod, Ankrd12, Golga1, Gpbp1, Hist3h2a, Rapgef2, or Sned1.

The activity of the oligonucleotide in reducing the expression or abundance of miR-145 may be determined in vitro and/or in vivo. For example, when inhibition of miR-145 activity is determined in vitro, the activity may be determined using a dual luciferase assay. The dual luciferase assay, as exemplified by the commercially available product PsiCHECK™ (Promega), involves placement of the miR recognition site in the 3' UTR of a gene for a detectable protein (e.g., renilla luciferase). The construct is co-expressed with miR-145, such that inhibitor activity can be determined by change in signal. A second gene encoding a detectable protein (e.g., firefly luciferase) can be included on the same plasmid, and the ratio of signals determined as an indication of the antimiR-145 activity of a candidate oligonucleotide. The oligonucleotide significantly inhibits such activity, as determined in the dual luciferase activity, at a concentration of about 50 nM or less, or in other embodiments, about 40 nM or less, about 20 nM or less, or about 10 nM or less. For example, the oligonucleotide may have an IC50 for inhibition of miR-145 activity of about 50 nM or less, about 40 nM or less, about 30 nM or less, or about 20 nM or less, as determined in the dual luciferase assay.

Alternatively, or in addition, the activity of the oligonucleotide in reducing the expression or abundance of miR-145 may be determined in a suitable mouse or rat model, where inhibition (e.g., by at least about 50%) of miR-145 expression is observed at an oligonucleotide dose, such as a dose of about 50 mg/kg or less, about 25 mg/kg or less, about 10 mg/kg or less or about 5 mg/kg or less. In some embodiments, the activity of the oligonucleotide is determined in an animal model, such as described in WO 2008/016924, which descriptions are hereby incorporated by reference. For example, the oligonucleotide may exhibit at least 50% inhibition of miR-145, such as a dose of about 50 mg/kg or less, about 25 mg/kg or less, about 10 mg/kg or less or about 5 mg/kg or less. In such embodiments, the oligonucleotide may be dosed intravenously or subcutaneously to mice, and the oligonucleotide may be formulated in saline.

The in vivo efficacy of the oligonucleotide may also be determined in a suitable mouse or rat model. The oligonucleotide may exhibit at least about 50% miR-145 target de-repression, such as at a dose of 50 mg/kg or less, 25 mg/kg or less, 10 mg/kg or less or 5 mg/kg or less. In some embodiments, the increased expression or fold-change of a miR-145 target gene in a cell or tissue relative to a saline control may also be determined in a suitable mouse or rat model. The oligonucleotide may exhibit at least about 1.1, about 1.2, about 1.3, about 1.4, or about 1.5 fold increase in expression of a miR-145 target, such as a dose of 50 mg/kg or less, 25 mg/kg or less, 10 mg/kg or less or 5 mg/kg or less. The p-value for the increase in expression or fold-change of a miR-145 target in a cell or tissue can be <0.05 or <0.01. The miR-145 target can be Klf4. Klf5, Lrrc71, Nedd41, Igf1r, Sec1412, Megf6, Fmod, Ankrd12, Golga1, Gpbp1, Hist3h2a, Rapgef2, or Sned1.

In such embodiments, the oligonucleotide may be dosed intravenously or subcutaneously to mice, and the oligonucleotide may be formulated in saline. The oligonucleotide with a specific LNA/DNA pattern can have increased in vivo efficacy in a particular tissue, such as the lung as compared to an oligonucleotide with the same nucleotide sequence but different LNA/DNA pattern. In some embodiments, the oligonucleotide with a specific LNA/DNA pattern increases the expression of a miR-145 target gene in a cell or tissue relative to a saline control. In yet other embodiments, a cell treated with an oligonucleotide with a specific LNA/DNA pattern has a greater than 1.0 fold-change in the expression of a miR-145 target gene relative to a cell treated with a saline control.

In these or other embodiments, the oligonucleotides of the present invention can be stable after administration, being detectable in the circulation and/or target organ for at least three weeks, at least four weeks, at least five weeks, or at least six weeks, or more, following administration. Thus, the oligonucleotides of the present invention may provide for less frequent administration, lower doses, and/or longer duration of therapeutic effect.

Generally, the length of the oligonucleotide and number and position of locked nucleotides is such that the oligonucleotide reduces miR-145 expression or abundance. In some embodiments, the length of the oligonucleotide and number and position of locked nucleotides is such that the oligonucleotide reduces miR-145 expression or abundance at an oligonucleotide concentration of about 50 nM or less in the in vitro luciferase assay, or at a dose of about 50 mg/kg or less, or about 25 mg/kg or less in a suitable mouse or rat model, each as described. In some embodiments, the length of the oligonucleotide and number and position of locked nucleotides is such that the oligonucleotide reduces miR-145 activity as determined by target de-repression, at a dose of about 50 mg/kg or less, or about 25 mg/kg or less in a suitable mouse or rat model, such as described herein.

The oligonucleotide of the present invention contains one or more locked nucleic acid (LNAs) residues, or "locked nucleotides." LNAs are described, for example, in U.S. Pat. Nos. 6,268,490, 6,316,198, 6,403,566, 6,770,748, 6,998, 484, 6,670,461, and 7,034,133, all of which are hereby incorporated by reference in their entireties. LNAs are modified nucleotides or ribonucleotides that contain an extra bridge between the 2' and 4' carbons of the ribose sugar moiety resulting in a "locked" conformation, and/or bicyclic structure. In one embodiment, the oligonucleotide contains one or more LNAs having the structure shown by structure A below. Alternatively or in addition, the oligonucleotide may contain one or more LNAs having the structure shown by structure B below. Alternatively or in addition, the oligonucleotide contains one or more LNAs having the structure shown by structure C below.

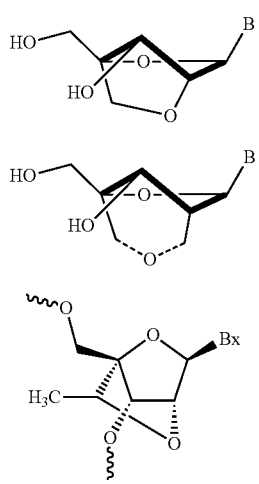

Other suitable locked nucleotides that can be incorporated in the oligonucleotides of the present invention include those described in U.S. Pat. Nos. 6,403,566 and 6,833,361, both of which are hereby incorporated by reference in their entireties.

In exemplary embodiments, the locked nucleotides have a 2' to 4' methylene bridge, as shown in structure A, for example. In other embodiments, the bridge comprises a methylene or ethylene group, which may be substituted, and which may or may not have an ether linkage at the 2' position.

The oligonucleotide may comprise, consist essentially of, or consist of, an antisense sequence to miR-145. In one embodiment, the oligonucleotide comprises an antisense sequence directed to miR-145. For example, the oligonucleotide can comprise a sequence that is at least partially complementary to a mature miR-145 sequence, e.g. at least about 75%, about 80%, about 85%, about 90%, about 95%, about 96%, about 97%, about 98%, or about 99% complementary to a human mature miR-145 sequence. In one embodiment, the antisense oligonucleotide comprises a sequence that is 100% complementary to a mature miR-145 sequence.

In certain embodiments, the oligonucleotide comprises a nucleotide sequence that is completely complementary to a nucleotide sequence of miR-145. In particular embodiments, the oligonucleotide comprises, consists essentially of, or consists of the nucleotide sequence complementary to miR-145. In this context, "consists essentially of" includes the optional addition of nucleotides (e.g., one or two) on either or both of the 5' and 3' ends, so long as the additional nucleotide(s) do not substantially affect (as defined by an increase in IC50 of no more than about 20%) the oligonucleotide's inhibition of the target miRNA activity in the dual luciferase assay or mouse model.

The oligonucleotide may comprise, consist essentially of, or consist of, an antisense sequence to miR-145 that comprises a sequence complementary to the seed region of miR-145. The seed region is the 5' portion of a miRNA spanning bases 2-8, i.e. 5'-UCCAGUUU-3' (SEQ ID NO: 7) for human mature miR-145. The sequence complementary to the seed region of miR-145 can be substantially or completely complementary to the seed region of miR-145, wherein a substantially complementary sequence may have from 1 to 4 mismatches (e.g., 1 or 2 mismatches).

The oligonucleotide generally has a nucleotide sequence designed to target mature miR-145. The oligonucleotide may, in these or other embodiments, also or alternatively be designed to target the pre- or pri-miRNA forms of miR-145. In certain embodiments, the oligonucleotide may be designed to have a sequence containing from 1 to 5 (e.g., 1, 2, 3, or 4) mismatches relative to the fully complementary (mature) miR-145 sequence. In certain embodiments, such antisense sequences may be incorporated into shRNAs or other RNA structures containing stem and loop portions, for example.

The oligonucleotide can be from about 8 to about 20 nucleotides in length, from about 15 to about 50 nucleotides in length, from about 18 to about 50 nucleotides in length, from about 10 to about 18 nucleotides in length, or from about 11 to about 16 nucleotides in length. The oligonucleotide in some embodiments is about 8, about 9, about 10, about 11, about 12, about 13, about 14, about 15, about 16, about 17, or about 18 nucleotides in length. In some embodiments, the oligonucleotide is at least about 16 nucleotides in length.

Generally, the number and position of LNA is such that the oligonucleotide reduces miR-145 activity. In one embodiment, the number and position of LNAs is such that the oligonucleotide has increased in vivo efficacy as compared to an oligonucleotide with a different number and/or position of LNAs. In some embodiments, the number and position of LNAs is such that the oligonucleotide increases the expression of a miR-145 target gene in a cell or tissue relative to a saline control. In yet other embodiments, the number and position of LNAs is such that a cell treated with the oligonucleotide has a greater than 1.0 fold-change in the expression of a miR-145 target gene relative to a cell treated with a saline control.

In certain embodiments, the oligonucleotide does not contain a stretch of nucleotides with more than four, or more than three, contiguous LNAs. For example, the oligonucleotide comprises no more than three contiguous LNAs. In these or other embodiments, the oligonucleotide can comprise a region or sequence that is substantially or completely complementary to the miR-145 seed region, in which the region or sequence comprises at least one, two, three, four, five, or six locked nucleic acids (LNAs).

The oligonucleotide generally contains at least 5, at least 7, or at least 9 LNAs. In various embodiments, the oligonucleotide is not fully comprised of LNAs. In some embodiments, the oligonucleotide comprises a mix of LNA and non-locked nucleotides. For example, the oligonucleotide may contain at least five or at least seven or at least nine locked nucleotides, and at least one non-locked nucleotide. In various embodiments, the oligonucleotide contains at least nine locked nucleotides. For example, the oligonucleotide may contain at least nine locked nucleotides and at least seven non-locked nucleotides.

The oligonucleotide of the present invention can comprise at least five LNAs, a LNA at the 5' end of the sequence, a LNA at the 3' end of the sequence, or any combination thereof. In one embodiment, the oligonucleotide comprises at least five LNAs, a LNA at the 5' end of the sequence, a LNA at the 3' end of the sequence, or any combination thereof, wherein three or fewer of the nucleotides are contiguous LNAs. For example, the oligonucleotide comprises no more than three contiguous LNAs. The oligonucleotide may comprise a sequence with at least five LNAs, a LNA at the 5' end, a LNA at the 3' end, and no more than three contiguous LNAs. The oligonucleotide may comprise a sequence with at least five LNAs, a LNA at the 5' end, a LNA at the 3' end, and no more than three contiguous LNAs, wherein the sequence is at least 16 nucleotides in length.

In some embodiments, the oligonucleotide comprises a 16-mer, wherein the 16-mer consists of sixteen nucleotides. In some embodiments, the 16-mer includes a sequence complementary to the seed region of miR-145. The 16-mer can comprise at least nine LNAs. In some embodiments, the 16-mer contains nine LNAs and seven non-locked nucleotides. In some embodiments, from the 5'end to the 3' end of the 16-mer, positions 1, 5, 6, 9, 10, 11, 13, 15, and 16; positions 1, 2, 6, 8, 10, 11, 13, 15, and 16; positions 1, 5, 6, 8, 10, 11, 13, 14, and 16; positions 1, 3, 4, 5, 6, 8, 10, 13, and 16; positions 1, 3, 4, 7, 8, 10, 12, 14, and 16; positions 1, 2, 6, 7, 10, 11, 12, 14, and 16; positions 1, 3, 5, 7, 9, 11, 13, 15, and 16; positions 1, 4, 5, 7, 9, 10, 12, 14, and 16; or positions 1, 5, 6, 8, 10, 11, 13, 15, and 16; of the 16-mer are LNAs. The 16-mer can be substantially or completely complementary to miR-145, wherein a substantially complementary sequence may have from 1 to 4 mismatches (e.g., 1 or 2 mismatches). In some embodiments, the oligonucleotide is selected from Table 1, such as M-10934, M-11239, M-11241, M-11242, M-11244, M-11318, M-11319, M-11320, or M-11321.

For non-locked nucleotides, the nucleotide may contain a 2' modification with respect to a 2' hydroxyl. For example, the 2' modification may be 2' deoxy. Incorporation of 2'-modified nucleotides in antisense oligonucleotides may increase both resistance of the oligonucleotides to nucleases and their thermal stability with complementary RNA. Various modifications at the 2' positions may be independently selected from those that provide increased nuclease sensitivity, without compromising molecular interactions with the RNA target or cellular machinery. Such modifications may be selected on the basis of their increased potency in vitro or in vivo. Exemplary methods for determining increased potency (e.g., IC50) for miR-145 inhibition are described herein, including the dual luciferase assay and in vivo miR-145 expression or target de-repression.

In some embodiments the 2' modification may be independently selected from O-alkyl (which may be substituted), halo, and deoxy (H). Substantially all, or all, nucleotide 2' positions of the non-locked nucleotides may be modified in certain embodiments, e.g., as independently selected from O-alkyl (e.g., O-methyl), halo (e.g., fluoro), deoxy (H), and amino. For example, the 2' modifications may each be independently selected from O-methyl and fluoro. In exemplary embodiments, purine nucleotides each have a 2' OMe and pyrimidine nucleotides each have a 2'-F. In certain embodiments, from one to about five 2' positions, or from about one to about three 2' positions are left unmodified (e.g., as 2' hydroxyls).

2' modifications in accordance with the invention also include small hydrocarbon substituents. The hydrocarbon substituents include alkyl, alkenyl, alkynyl, and alkoxyalkyl, where the alkyl (including the alkyl portion of alkoxy), alkenyl and alkynyl may be substituted or unsubstituted. The alkyl, alkenyl, and alkynyl may be C1 to C10 alkyl, alkenyl or alkynyl, such as C1, C2, or C3. The hydrocarbon substituents may include one or two or three non-carbon atoms, which may be independently selected from N, O, and/or S.

The 2' modifications may further include the alkyl, alkenyl, and alkynyl as O-alkyl, O-alkenyl, and O-alkynyl.

Exemplary 2' modifications in accordance with the invention include 2'-O-alkyl (C1-3 alkyl, such as 2'OMe or 2'OEt), 2'-O-methoxyethyl (2'-O-MOE), 2'-O-aminopropyl (2'-O-AP), 2'-O-dimethylaminoethyl (2'-O-DMAOE), 2'-O-dimethylaminopropyl (2'-O-DMAP), 2'-O-dimethylaminoethyloxyethyl (2'-O-DMAEOE), or 2'-O—N-methylacetamido (2'-O-NMA) substitutions.

In certain embodiments, the oligonucleotide contains at least one 2'-halo modification (e.g., in place of a 2' hydroxyl), such as 2'-fluoro, 2'-chloro, 2'-bromo, and 2'-iodo. In some embodiments, the 2' halo modification is fluoro. The oligonucleotide may contain from 1 to about 5 2'-halo modifications (e.g., fluoro), or from 1 to about 3 2'-halo modifications (e.g., fluoro). In some embodiments, the oligonucleotide contains all 2'-fluoro nucleotides at non-locked positions, or 2'-fluoro on all non-locked pyrimidine nucleotides. In certain embodiments, the 2'-fluoro groups are independently di-, tri-, or un-methylated.

The oligonucleotide may have one or more 2'-deoxy modifications (e.g., H for 2' hydroxyl), and in some embodiments, contains from 2 to about 10 2'-deoxy modifications at non-locked positions, or contains 2'deoxy at all non-locked positions.

In exemplary embodiments, the oligonucleotide contains 2' positions modified as 2'OMe in non-locked positions. Alternatively, non-locked purine nucleotides are modified at the 2' position as 2'OMe, with non-locked pyrimidine nucleotides modified at the 2' position as 2'-fluoro.

In certain embodiments, the oligonucleotide further comprises at least one terminal modification or "cap." The cap may be a 5' and/or a 3'-cap structure. The terms "cap" or "end-cap" include chemical modifications at either terminus of the oligonucleotide (with respect to terminal ribonucleotides), and includes modifications at the linkage between the last two nucleotides on the 5' end and the last two nucleotides on the 3' end. The cap structure as described herein may increase resistance of the oligonucleotide to exonucleases without compromising molecular interactions with the miRNA target (i.e. miR-145) or cellular machinery. Such modifications may be selected on the basis of their increased potency in vitro or in vivo. The cap can be present at the 5'-terminus (5'-cap) or at the 3'-terminus (3'-cap) or can be present on both ends. In certain embodiments, the 5'- and/or 3'-cap is independently selected from phosphorothioate monophosphate, abasic residue (moiety), phosphorothioate linkage, 4'-thio nucleotide, carbocyclic nucleotide, phosphorodithioate linkage, inverted nucleotide or inverted abasic moiety (2'-3' or 3'-3'), phosphorodithioate monophosphate, and methylphosphonate moiety. The phosphorothioate or phosphorodithioate linkage(s), when part of a cap structure, are generally positioned between the two terminal nucleotides on the 5' end and the two terminal nucleotides on the 3' end.

In certain embodiments, the oligonucleotide has at least one terminal phosphorothioate monophosphate. The phosphorothioate monophosphate may support a higher potency by inhibiting the action of exonucleases. The phosphorothioate monophosphate may be at the 5' and/or 3' end of the oligonucleotide. A phosphorothioate monophosphate is defined by the following structures, where B is base, and R is a 2' modification as described above:

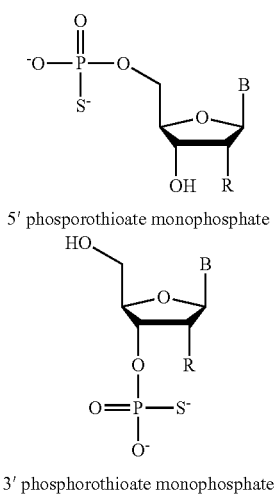

5' phosporothioate monophosphate

3' phosphorothioate monophosphate

Where the cap structure can support the chemistry of a locked nucleotide, the cap structure may incorporate a LNA as described herein.

Phosphorothioate linkages may be present in some embodiments, such as between the last two nucleotides on the 5' and the 3' end (e.g., as part of a cap structure), or as alternating with phosphodiester bonds. In these or other embodiments, the oligonucleotide may contain at least one terminal abasic residue at either or both the 5' and 3' ends. An abasic moiety does not contain a commonly recognized purine or pyrimidine nucleotide base, such as adenosine, guanine, cytosine, uracil or thymine. Thus, such abasic moieties lack a nucleotide base or have other non-nucleotide base chemical groups at the 1' position. For example, the abasic nucleotide may be a reverse abasic nucleotide, e.g., where a reverse abasic phosphoramidite is coupled via a 5' amidite (instead of 3' amidite) resulting in a 5'-5' phosphate bond. The structure of a reverse abasic nucleoside for the 5' and the 3' end of a polynucleotide is shown below.

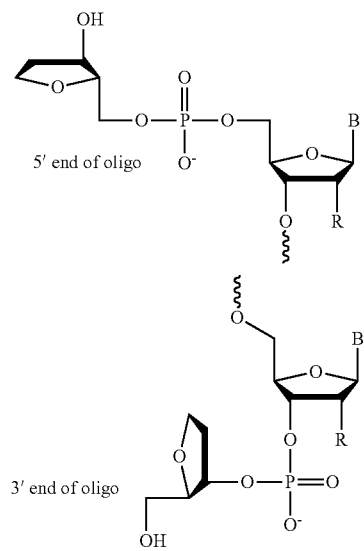

The oligonucleotide may contain one or more phosphorothioate linkages. Phosphorothioate linkages have been used to render oligonucleotides more resistant to nuclease cleavage. For example, the polynucleotide may be partially phosphorothioate-linked, for example, phosphorothioate linkages may alternate with phosphodiester linkages. In certain embodiments, however, the oligonucleotide is fully phosphorothioate-linked. In other embodiments, the oligonucleotide has from one to five or one to three phosphate linkages.

In some embodiments, the nucleotide has one or more carboxamido-modified bases as described in PCT/US11/59588, which is hereby incorporated by reference, including with respect to all exemplary pyrimidine carboxamido modifications disclosed therein with heterocyclic substituents.

The synthesis of oligonucleotides, including modified polynucleotides, by solid phase synthesis is well known and is reviewed in *New Chemical Methods for Synthesizing Polynucleotides*. Caruthers M H, Beaucage S L, Efcavitch J W, Fisher E F, Matteucci M D, Stabinsky Y. Nucleic Acids Symp. Ser. 1980; (7):215-23.

The oligonucleotide may be incorporated within a variety of macromolecular assemblies or compositions. Such complexes for delivery may include a variety of liposomes, nanoparticles, and micelles, formulated for delivery to a patient. The complexes may include one or more fusogenic or lipophilic molecules to initiate cellular membrane penetration. Such molecules are described, for example, in U.S. Pat. No. 7,404,969 and U.S. Pat. No. 7,202,227, which are hereby incorporated by reference in their entireties. Alternatively, the oligonucleotide may further comprise a pendant lipophilic group to aid cellular delivery, such as those described in WO 2010/129672, which is hereby incorporated by reference.

The present invention also provides a method for delivering an oligonucleotide disclosed herein to a cell (e.g., as part of a composition or formulation described herein) for reducing or inhibiting activity of miR-145 in the cell. The cell can be a smooth muscle cell. Also provided herein is a method for inhibiting smooth muscle cell proliferation comprising contacting a smooth muscle cell with an oligonucleotide disclosed herein. The cell can be a mammalian cell. In some embodiments, the cell is a lung or cardiac cell. The cell can be in vivo or ex vivo.

Also provided herein is a method for treating, ameliorating, or preventing the progression of a condition in a subject comprising administering a pharmaceutical composition comprising an oligonucleotide disclosed herein. The method generally comprises administering the oligonucleotide or composition comprising the same to a subject. The term "subject" or "patient" refers to any vertebrate including, without limitation, humans and other primates (e.g., chimpanzees and other apes and monkey species), farm animals (e.g., cattle, sheep, pigs, goats and horses), domestic mammals (e.g., dogs and cats), laboratory animals (e.g., rodents such as mice, rats, and guinea pigs), and birds (e.g., domestic, wild and game birds such as chickens, turkeys and other gallinaccous birds, ducks, geese, and the like). In some embodiments, the subject is a mammal. In other embodiments, the subject is a human.

The subject may have a condition associated with, mediated by, or resulting from, expression of miR-145, such as neointima formation or restenosis. MiR-145 is enriched in smooth muscle tissue and can regulate smooth muscle proliferation. In one embodiment, a method for inhibiting or reducing neointima formation or restenosis, such as after vessel injury, comprises administering the oligonucleotide or composition comprising the same to a subject in need thereof.

In another embodiment, the condition is pulmonary arterial hypertension (PAH). In one embodiment, the present invention provides a method of treating or preventing pulmonary hypertension, particularly PAH, in a subject in need thereof comprising administering to the subject an inhibitor of miR-145 expression and/or activity. Pulmonary hypertension results when pulmonary arteries in the lungs become narrowed, blocked, or damaged causing an increase in arterial pressure. The enhanced workload on the right ventricle causes strain on the heart muscle and can lead to heart failure. Symptoms of PAH include, but are not limited to, shortness of breath, initially while exercising and eventually while at rest, fatigue, dizziness or fainting spells, chest pressure or pain, swelling in lower extremities (ankles and legs) and abdomen, bluish color to skin and lips, and racing pulse or heart palpitations. Preferably, one or more of the aforesaid symptoms is improved or eliminated, or development of PAH is retarded, in a subject suffering from PAH following administration of the miR-145 inhibitor as compared to a subject not receiving treatment. In some embodiments, the right ventricular systolic pressure in the subject is reduced following administration of the miR-145 inhibitor.

Forms of pulmonary hypertension that can be treated with the methods of the invention include, but are not limited to, idiopathic PAH, hereditary or familial PAH, and secondary pulmonary hypertension (e.g. hypertension resulting from pulmonary emboli, emphysema, pulmonary fibrosis, and congenital heart disease). Familial or hereditary forms of PAH have been linked to mutations in certain genes. For instance, 70% of patients with the heritable form of PAH have mutations in the gene encoding bone morphogenetic protein (BMP) type-2 receptor (BMPR2) (Morrell et al., 2001). Thus, in some embodiments, the subject to be treated with the methods of the invention is at risk for developing PAH. In one embodiment, the subject (e.g. a human) at risk has a mutation in the gene encoding for BMPR2.

In another embodiment, the condition is hypertension, including systemic hypertension. The hypertension can be any type, including primary or essential hypertension, secondary hypertension, malignant hypertension, isolated systolic hypertension, or resistant hypertension. Primary hypertension is the most common type and does not appear to have an identifiable cause. Secondary hypertension is generally caused by reversible factors. In some embodiments, secondary hypertension is caused by kidney damage, a tumor, overactivity of the adrenal gland, thyroid dysfunction, coarctation of the aorta, a pregnancy-related condition, sleep apnea, a drug, food, or drink. Malignant hypertension is the most severe form and can be progressive. In some cases, malignant hypertension can lead to heart failure, kidney damage or brain hemorrhage, or death. Generally, malignant hypertension is not caused by a cancer or malignancy. Isolated systolic hypertension is when the systolic blood pressure is consistently above 160 mm Hg, and the diastolic below 90 mm Hg, and may be from age-related loss of elasticity in the arteries, which can be due to arteriosclerosis. Hypertension is typically typed as resistant hypertension when blood pressure cannot be reduced to below 140/99 mmHg, despite a triple-drug regime.

In one embodiment, the present invention provides a method for treating or preventing hypertension, such as primary hypertension, secondary hypertension, malignant hypertension, isolated systolic hypertension, or resistant hypertension, in a subject in need thereof comprising administering to the subject an inhibitor of miR-145 expression and/or activity.

The present invention further provides pharmaceutical compositions comprising an oligonucleotide disclosed herein. Where clinical applications are contemplated, pharmaceutical compositions will be prepared in a form appropriate for the intended application. Generally, this will entail preparing compositions that are essentially free of pyrogens, as well as other impurities that could be harmful to humans or animals.

In one embodiment, the pharmaceutical composition comprises an effective dose of a miR-145 inhibitor and a pharmaceutically acceptable carrier. For instance, the pharmaceutical composition comprises an effective dose or amount of an oligonucleotide of the present invention or a pharmaceutically-acceptable salt thereof, and a pharmaceutically-acceptable carrier or diluent. The oligonucleotide can be selected from Table 1, such as M-10934, M-11239, M-11241, M-11242, M-11244, M-11318, M-11319, M-11320, or M-11321.

An "effective dose" is an amount sufficient to effect a beneficial or desired clinical result. An effective dose of an oligonucleotide disclosed herein may be from about 0.001 mg/kg to about 100 mg/kg, about 0.01 mg/kg to about 10 mg/kg, about 0.1 mg/kg to about 10 mg/kg, about 1 mg/kg to about 10 mg/kg, about 2.5 mg/kg to about 50 mg/kg, or about 5 mg/kg to about 25 mg/kg. The precise determination of what would be considered an effective dose may be based on factors individual to each patient, including their size, age, type and severity of pulmonary arterial hypertension, and nature of the oligonucleotide (e.g. melting temperature, LNA content, etc.). Therefore, dosages can be readily ascertained by those of ordinary skill in the art from this disclosure and the knowledge in the art. In some embodiments, the methods comprise administering an effective dose of the pharmaceutical composition 1, 2, 3, 4, 5, or 6 times a day. In some embodiments, administration is 1, 2, 3, 4, or 5 times a week. In other embodiments, administration is biweekly or monthly.

Colloidal dispersion systems, such as macromolecule complexes, nanocapsules, nanoparticles, microspheres, beads, and lipid-based systems including oil-in-water emulsions, micelles, mixed micelles, and liposomes, may be used as delivery vehicles for the oligonucleotide inhibitors of miR-145 function. In certain embodiments, the miR-145 inhibitors are formulated for pulmonary delivery. As used herein "pulmonary delivery" or "respiratory delivery" refer to delivery of miR-145 inhibitors to a subject by inhalation through the mouth or nose and into the lungs. For example, the miR-145 inhibitors can be formulated as a snuff, aerosol, solution for a nebulizer, or as a microfine powder for insufflation. In embodiments in which the miR-145 inhibitor is formulated as a dry powder, the particles of active compound can have diameters of less than 50 microns, preferably less than 10 microns, such as between 1 and 5 microns or between 2 and 5 microns.

One will generally desire to employ appropriate salts and buffers to render delivery vehicles stable and allow for uptake by target cells. Aqueous compositions of the present invention comprise an effective amount of the delivery vehicle comprising the inhibitor polynucleotides (e.g. liposomes or other complexes or expression vectors) dissolved or dispersed in a pharmaceutically acceptable carrier or aqueous medium. The phrases "pharmaceutically acceptable" or "pharmacologically acceptable" refers to molecular entities and compositions that do not produce adverse, allergic, or other untoward reactions when administered to an animal or a human. As used herein, "pharmaceutically acceptable carrier" includes solvents, buffers, solutions, dispersion media, coatings, antibacterial and antifungal agents, isotonic and absorption delaying agents and the like acceptable for use in formulating pharmaceuticals, such as pharmaceuticals suitable for administration to humans. The use of such media and agents for pharmaceutically active substances is well known in the art. Except insofar as any conventional media or agent is incompatible with the active ingredients of the present invention, its use in therapeutic compositions is contemplated. Supplementary active ingredients also can be incorporated into the compositions, provided they do not inactivate the oligonucleotides of the compositions.

The active compositions of the present invention may include classic pharmaceutical preparations. Administration of these compositions according to the present invention may be via any common route so long as the target tissue is available via that route. This includes oral, nasal, or buccal. Alternatively, administration may be by intradermal, subcutaneous, intramuscular, intraperitoneal, intraarterial, or intravenous injection. In some embodiments, the pharmaceutical composition is directed injected into lung or cardiac tissue.

In certain embodiments, pharmaceutical compositions comprising miR-145 inhibitors are administered by inhalation. Pharmaceutical compositions comprising a miR-145 inhibitor may also be administered by catheter systems or systems that isolate coronary/pulmonary circulation for delivering therapeutic agents to the heart and lungs. Various catheter systems for delivering therapeutic agents to the heart and coronary vasculature are known in the art. Some non-limiting examples of catheter-based delivery methods or coronary isolation methods suitable for use in the present invention are disclosed in U.S. Pat. No. 6,416,510; U.S. Pat. No. 6,716,196; U.S. Pat. No. 6,953,466, WO 2005/082440. WO 2006/089340, U.S. Patent Publication No. 2007/0203445, U.S. Patent Publication No. 2006/0148742, and U.S. Patent Publication No. 2007/0060907, which are all herein incorporated by reference in their entireties. Such compositions would normally be administered as pharmaceutically acceptable compositions as described herein.

The active compounds may also be administered parenterally or intraperitoneally. By way of illustration, solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations generally contain a preservative to prevent the growth of microorganisms.

The pharmaceutical forms suitable for injectable use, catheter delivery, or inhalational delivery include, for example, sterile aqueous solutions or dispersions and sterile powders for the extemporaneous preparation of sterile injectable solutions or dispersions (e.g. aerosols, nebulizer solutions). Generally, these preparations are sterile and fluid to the extent that easy injectability or aerosolization/nebulization exists. Preparations should be stable under the conditions of manufacture and storage and should be preserved against the contaminating action of microorganisms, such as bacteria and fungi. Appropriate solvents or dispersion media may contain, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial an antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions may be prepared by incorporating the active compounds in an appropriate amount into a solvent along with any other ingredients (for example as enumerated above) as desired, followed by filtered sterilization. Generally, dispersions are prepared by incorporating the various sterilized active ingredients into a sterile vehicle which contains the basic dispersion medium and the desired other ingredients, e.g., as enumerated above. In the case of sterile powders for the preparation of sterile injectable solutions, the preferred methods of preparation include vacuum-drying and freeze-drying techniques which yield a powder of the active ingredient(s) plus any additional desired ingredient from a previously sterile-filtered solution thereof. In some embodiments, sterile powders can be administered directly to the subject (i.e. without reconstitution in a diluent), for example, through an insufflator or inhalation device.

The compositions of the present invention generally may be formulated in a neutral or salt form. Pharmaceutically-acceptable salts include, for example, acid addition salts (formed with the free amino groups of the protein) derived from inorganic acids (e.g., hydrochloric or phosphoric acids), or from organic acids (e.g., acetic, oxalic, tartaric, mandelic, and the like). Salts formed with the free carboxyl groups of the protein can also be derived from inorganic bases (e.g., sodium, potassium, ammonium, calcium, or ferric hydroxides) or from organic bases (e.g., isopropylamine, trimethylamine, histidine, procaine and the like).

Upon formulation, solutions are preferably administered in a manner compatible with the dosage formulation and in such amount as is therapeutically effective. The formulations may easily be administered in a variety of dosage forms such as injectable solutions, drug release capsules, unit dose inhalers, and the like. For parenteral administration in an aqueous solution, for example, the solution generally is suitably buffered and the liquid diluent first rendered isotonic for example with sufficient saline or glucose. Such aqueous solutions may be used, for example, for intravenous, intramuscular, subcutaneous, intraarterial, and intraperitoneal administration. Preferably, sterile aqueous media are employed as is known to those of skill in the art, particularly in light of the present disclosure. By way of illustration, a single dose may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

The composition or formulation may employ a plurality of therapeutic oligonucleotides, including at least one described herein. For example, the composition or formulation may employ at least 2, 3, 4, or 5 miR-145 inhibitors described herein. In another embodiment, an oligonucleotide of the present invention may be used in combination with other therapeutic modalities. Combinations may also be achieved by contacting a cell with more than one distinct composition or formulation, at the same time. Alternatively, combinations may be administered sequentially.

In one embodiment of the present invention, an antimiR-145 is used in combination with other therapeutic modalities. Examples of combination therapies include any of the foregoing. Combinations may be achieved with a single composition or pharmacological formulation that includes both agents, or with two distinct compositions or formulations, at the same time, wherein one composition includes the antimiR-145 and one more other agents. Alternatively, the therapy using an antimiR-145 may precede or follow administration of the other agent(s) by intervals ranging from minutes to weeks. In embodiments where the other agent and antimiR-145 are applied separately to the cell, one would generally ensure that a significant period of time did not expire between the time of each delivery, such that the agent and the antimiR-145 would still be able to exert an advantageously combined effect on the cell. In such instances, it is contemplated that one would typically contact the cell with both modalities within about 12-24 hours of each other, within about 6-12 hours of each other, or with a delay time of only about 12 hours. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

In one embodiment, more than one administration of the antimiR-145 or the other agent(s) will be desired. In this regard, various combinations may be employed. By way of illustration, where the antimiR-145 is "A" and the other agent is "B," the following permutations based on 3 and 4 total administrations are provided as examples: A/B/A, B/A/B, B/B/A, A/A/B, B/A/A, A/B/B, B/B/B/A, B/B/A/B. A/A/B/B, A/B/A/B, A/B/B/A, B/B/A/A, B/A/B/A, B/A/A/B, B/B/B/A, A/A/A/B. B/A/A/A, A/B/A/A, A/A/B/A, A/B/B/B, B/A/B/B, BIB/A/B. Other combinations are likewise contemplated. Specific examples of other agents and therapies are provided below.

In one embodiment of the present invention, the method of inhibiting, preventing, or treating restenosis or neointima formation in a subject in need thereof comprises administering to the subject a miR-145 inhibitor, such as an antimiR-145 as described herein, and another agent that inhibits restenosis or neointima formation. Cardiologists have tried a number of approaches to decrease the risk of restenosis. Stenting is becoming more commonplace, replacing balloon angioplasty. During the stenting procedure, a metal mesh (stent) is deployed against the wall of the artery revascularizing the artery. Other approaches include local radiotherapy and the use of immunosuppressive drugs, coated onto the stenting mesh. In one embodiment, a combination of different miR-145 inhibitors is administered, such as an antimiR-145 as described herein, and a small molecule inhibitor of miR-145. Thus, examples of combination therapies include any of the foregoing.

In one embodiment of the present invention, the method for inhibiting, preventing, or treating hypertension in a subject in need thereof comprises administering to the subject a miR-145 inhibitor, such as an antimiR-145 as described herein, and a second agent that inhibits, prevents or treats hypertension. In one embodiment, a combination of different miR-145 inhibitors is administered, such as an antimiR-145 as described herein, and a small molecule inhibitor of miR-145.

In one embodiment of the present invention, the method of inhibiting, preventing, or treating PAH in a subject in need thereof comprises administering to the subject a miR-145 inhibitor, such as an antimiR-145 as described herein, and a second agent that inhibits, prevents or treats PAH. In one embodiment, a combination of different miR-145 inhibitors is administered, such as an antimiR-145 as described herein, and a small molecule inhibitor of miR-145.

In one embodiment, the second or additional agent for inhibiting, preventing, or treating PAH is an agonist of miR-204. The human miR-204-5p sequence is 5'-UUC-CCUUUGUCAUCCUAUGCCU-3' (SEQ ID NO: 8). The human miR-204-3p sequence is 5'-GCUGGGAAGGCAAAGGGACGU-3' (SEQ ID NO: 9). An agonist of miR-204 can be a polynucleotide comprising a mature miR-204 sequence. In some embodiments, the polynucleotide comprises the sequence of the pri-miRNA or pre-miRNA sequence for miR-204. The polynucleotide comprising the mature miR-204, pre-miR-204, or pri-miR-204 sequence can be single stranded or double stranded. In one embodiment, the miR-204 agonist can be about 15 to about 50 nucleotides in length, about 18 to about 30 nucleotides in length, about 20 to about 25 nucleotides in length, or about 10 to about 14 nucleotides in length. The miR-204 agonist can be at least about 75%, about 80%, about 85%, about 90%, about 95%, about 96%, about 97%, about 98%, about 99%, or about 100% identical to the mature, pri-miRNA or pre-miRNA sequence of miR-204. In one embodiment, the miR-204 agonist has the sequence of SEQ ID NO: 15 or 16. The miR204 agonist that is a polynucleotide can contain one or more chemical modifications, such as locked nucleic acids, peptide nucleic acids, sugar modifications, such as 2'-O-alkyl (e.g. 2'-O-methyl, 2'-O-methoxyethyl), 2'-fluoro, and 4' thio modifications, and backbone modifications, such as one or more phosphorothioate, morpholino, or phosphonocarboxylate linkages. In one embodiment, the polynucleotide comprising a miR-204 sequence is conjugated to cholesterol. The polynucleotide comprising a miR-204 sequence can be expressed in vivo from a vector and/or operably linked to a promoter, such as described above.

In another embodiment, the agonist of miR-204 can be an agent distinct from miR-204 that acts to increase, supplement, or replace the function of miR-204. For instance, agents that inhibit PDGF, endothelin-1, angiotensin II, and STAT3 expression or activity can be used in combination with a miR-145 inhibitor for treating, preventing or preventing PAH. The agent may be delivered in the form of a polypeptide, peptide, small organic molecule, nucleic acid encoding a polypeptide of interest, and the like. A polypeptide may be any translation product of a nucleic acid regardless of size and glycosylation. An agent may also be in the form of a simple drug, peptide, peptide fragment, DNA. RNA, ribozyme or engineered hybrid of a nucleic acid and peptide or peptide fragment, or a derivative of each.

A combination for inhibiting, treating, preventing or preventing PAH, neointima formation or restenosis, or hypertension can also comprise an antimiR-145 and a blood vessel dilator (vasodilator), such as, but not limited to epoprostenol. Other agents that can be used with an antimiR-145 include, but are not limited to, an endothelin receptor antagonist, such as bosentan, sitaxentan, and ambriesentan; phosphodiesterase inhibitor, such as phosphodiesterase type 5 inhibitors, sildenafil and tadalafil; calcium channel blocker, such as amlodipine, diltiazem, and nifedipine; prostaglandin, such as treprostinil, iloprost and beraprost; isosorbide dinitrate; and guanylate cyclase activator, such as cinaciguat and riociguat.

An anticoagulant or compound that blocks or inhibits thrombin can also be used, such as, warfarin and compounds based on the tripeptide motif D-Phe-Pro-Arg; e.g., LY287045, etc. Many compounds, such as inogatran and melagatran, are known in the art and can also be used. For non-limiting examples, see U.S. Pat. Nos. 6,326,386; 6,232,315; 6,201,006; 6,174,855; 6,060,451; and 5,985,833; among others.

Additional agents that can be used with an antimiR-145 include an angiotensin converting enzyme inhibitor; nicotine receptor agonist; agent that increases concentrations of nitric oxide, anti-angiogenic agent; agonist of the TGF-β receptor; and death domain receptor ligand.

Angiotensin converting enzyme inhibitors (ACE-I) that can also be used in combination with a miR-145 inhibitor for treating, preventing or preventing PAH include, but are not limited to, captopril, benazepril, enalapril, fosinopril, lisinopril, quinapril, Ramipril, imidapril, perindopril, erbumine, and trandolapril. ACE receptor blockers may also be used in place of or as well as ACE inhibitors, and these include, but are not limited to, losartan, irbesartan, candesartan, cilexetil, and valsartan.

Nicotine receptor agonists, e.g., nicotine (S-3-(1-methyl-2-pyrrolidinyl)pyridine) and other compounds that substantially specifically bind a nicotine receptor and provide a pharmacological effect can also be used in combination with an antimiR-145, such as for treating, preventing or preventing PAH. Nicotine receptor agonists encompass naturally-occurring compounds (including, but not limited to, small molecules, polypeptides, peptides, and the like, such as naturally-occurring plant alkaloids), endogenous ligands (e.g., purified from a natural source, recombinantly produced, or synthetic, and further including derivatives and variants of such endogenous ligands), and synthetically produced compounds (e.g., small-molecules, peptides, etc.). The term "nicotine" further includes any pharmacologically acceptable derivative or metabolite of nicotine which: exhibits pharmacotherapeutic properties similar to nicotine. Such derivatives, metabolites, and derivatives of metabolites are known in the art, and include, but are not necessarily limited to, cotinine, norcotinine, nornicotine, nicotine N-oxide, cotinine N-oxide, 3-hydroxycotinine and 5-hydroxycotinine or pharmaceutically acceptable salts thereof.

An antimiR-145 can also be used with one or more agents that increase nitric oxide for treating, preventing or preventing PAH. Examples of nitric oxide promoting agents include, but are not limited to, S-nitrosopenicillamine, sodium nitroprusside, N-ethyl-2-(1-ethyl-2-hydroxy-2nitrosohydrazino) ethanamine (NOC 12), and others. The production of nitric oxide may also be modulated by cytokines, such as γ-interferon, tumor necrosis factor, IL-1, IL-2 and endotoxin due to their effect on the enzyme, nitric oxide synthase. The inducible form of NO synthase is increased by cytokines and the constitutive form seems to be decreased by cytokines. HMG-CoA reductase inhibitors have been found to upregulate endothelial cell NOS activity, as described by U.S. Pat. No. 6,147,109, Liao et al. Any of the forms of nitric oxide synthase can be utilized, as the protein or an active fragment derived therefrom, or as a DNA construct for expression.

Agents with an anti-angiogenic effect can also be used in combination with an antimiR-145, such as for treating, preventing or preventing PAH, neointima formation, restenosis, or hypertension. These include, but are not limited to the anti-angiogenic polypeptides: angiostatin: endostatin; and anti-angiogenic anti-thrombin III; and the like, and further include functionally active variants and derivatives thereof. Other anti-angiogenic agents include inhibitors of matrix metalloproteases, e.g., amifostine, WR-1065; marimastat, primomastat, a-1 antitrypsin; sphingosine and the like.

Agonists of the TGF-β receptor are also of interest. TGF-β receptor Type I and type II mediate most activities of TGF-β. Ligands include TGF-β, and mimetics and biologically active derivatives thereof.

Other agents of interest for use with an antimiR-14, such as for treating, preventing or preventing PAH include death domain receptor ligands, which are compounds, usually polypeptide compounds that bind to mammalian cell surface receptors comprising a death domain or homologs or orthologs thereof, and that, by binding so deliver a signal for apoptosis to the cell. The intracellular protein interactions triggered by these receptors can be attributed to binding interactions of the death domain, which is homologous to an approximately 80 amino acid domain near the C-terminus of TNF-R1, and is responsible for signaling cytotoxicity. The TNF receptor death domain family includes TNF-R1, Fas (CD95), TRAMP (wsl/Apo-3/DR-3), TRAIL-R1 (DR-4) and TRAIL-R2 (DR-5, TRICK2, KILLER). Death domain ligands include proteins that regulate cellular proliferation and differentiation by binding to specific death domain receptors. These ligands include the TNF family, e.g., TNF, lymphotoxin, CD30 ligand, 4-1 BB ligand, CD40 ligand, CD27 ligand, and TRAIL (TNF-related apoptosis-inducing ligand), and homologs and analogs thereof.

Analogues of rapamycin, such as tacrolimus (FK-506), sirolimus and everolimus, normally used as immunosuppressants but recently discovered to also inhibit the proliferation of vascular smooth muscle cells, may also be used in combination with an antimiR-145. Antisense knockdown of c-myc, a protein critical for progression of cell replication, is another approach to inhibit cell proliferation in the artery wall, and can be used in combination with a miR-145 inhibitor.

In one embodiment, covalent or non-covalent attachment of antiplatelet agents is also of interest, including GPIIb/IIIa inhibitors, e.g., RheoPro, which can be used in combination with a miR-145 inhibitor. Treatments or therapies such as oxygen therapy, can also be used in combination with administration of an antimiR-145.

The present invention also includes kits comprising an antimiR-145 described herein and an administration device. In certain embodiments, the administration device is a device designed to deliver the miR-145 inhibitor to the lungs through the nose or mouth, such as for the treatment or prevention of PAH. For instance, suitable administration devices for pulmonary delivery include, but are not limited to, droppers, swabs, aerosolizers, insufflators, nebulizers, inhalers (e.g., aerosol-based metered dose inhalers), dry powder dispersion devices, and other pulmonary delivery devices, including manually activated, gas propelled, sonic-driven, and the like. In some embodiments, the antimiR-145 is formulated as a powder contained within the administration device. In other embodiments, the antimiR-145 is formulated as a liquid aerosol contained within the administration device. In a particular embodiment, the administration device is an inhaler. In embodiments in which the antimiR-145 is to be delivered intravenously or intra-arterially, the kit can comprise a catheter or other like appropriate administration device. The kit may further comprise instructions for administering an effective dose of the anti-miR-145 to a subject to inhibit, treat or prevent pulmonary hypertension, neointima formation, restenosis, and/or hypertension. In some embodiments, the kit comprises one or more additional agents or therapies, such as described above.

This invention is further illustrated by the following additional examples that should not be construed as limiting. Those of skill in the art should, in light of the present disclosure, appreciate that many changes can be made to the specific embodiments which are disclosed and still obtain a like or similar result without departing from the spirit and scope of the invention.

EXAMPLES

Example 1. In Viva Efficacy of AntimiR-145 Compounds

To optimize the compound targeting miR-145 in the lung, an in vivo screen was performed using de-repression of direct mRNA targets of miR-145 in the lung, as a read-out for in vivo functionality.

In total 9 different antimiR designs were tested in rat, as depicted in Table 1:

a chemistry control. Lung tissue was collected 48 hours after injection. The mRNAs of Klf4, Klf5, Lrrc71, Nedd41, Igf1r, Sec1412, Megf6. Fmod, Ankrd12, Golga1. Gpbp1, Hist3h2a, Rapgef2, and Sned1 were measured by real time PCR in total lung RNA. The results are shown in FIG. 1 as fold-change values relative to saline-treated animals.

The results from these experiments showed that M-11318 had the highest efficacy, followed by M-11319, M-11321, and M-11239. M-11244 and M-11320 had similar efficacy and had lower efficacy than M-11239. Lastly, of the nine compounds, M-10934, M-11242, and M-11241 had the lowest efficacy.

Figure 2:
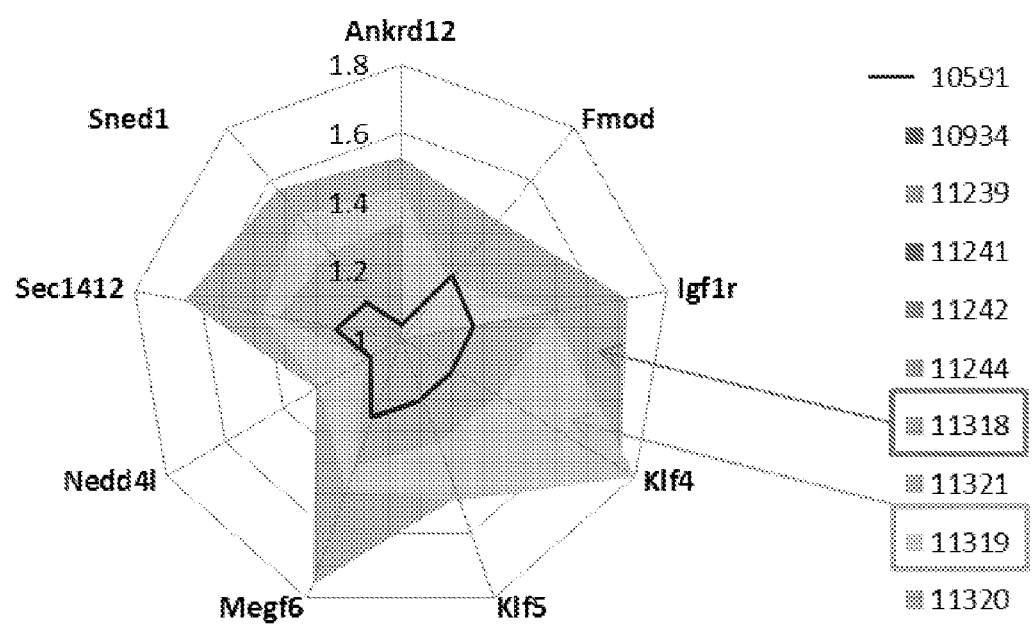
FIG. 2. Radar plots representing nine miR-145 gene targets and their fold-change for de-repression relative to saline. M-11318 shows the largest area representing the cumulative fold-change values for all nine genes shown. M-11319 is the second-largest area. The control oligonucleotide, M-10591, shown by the black line, has less target derepression activity compared to the active compounds.

Radar plots representing nine miR-145 gene targets and their fold-change for de-repression relative to saline are depicted in FIG. 2. M-11318 shows the largest area representing the cumulative fold-change values for all nine genes. M-11319 is the second-largest area. The control oligonucleotide M-10591, shown by the black line, has less target derepression activity compared to the active compounds.

Example 2. MiR-145 Specificity of AntimiR-145 Compound

Sprague-Dawley rats of 49 to 52 days of age were injected subcutaneously with saline or M-11318 at a dose of 25

TABLE 1

Inhibitor designs.

| | | | | | | | | | | | | | Seed Region | | | | | | | | SEQ ID NO: |
|---|---|---|---|---|---|---|---|---|---|---|---|---|---|---|---|---|---|---|---|---|---|
| miR-145 (3' to 5') | u | c | c | c | t | a | a | g | a | c | c | c | u | _u_ | _u_ | _u_ | g | _a_ | _c_ | _c_ | _u_ | g | 10 |
| miR-145 Reverse Complement (5' to 3') | a | g | g | g | a | t | t | c | c | t | g | g | g | a | _a_ | _a_ | _a_ | c | t | g | g | _a_ | c | 11 |

| M# | Position # | 1 | 2 | 3 | 4 | 5 | 6 | 7 | 8 | 9 | 10 | 11 | 12 | 13 | 14 | 15 | 16 | |
|---|---|---|---|---|---|---|---|---|---|---|---|---|---|---|---|---|---|---|
| 10934 | | T | c | c | t | G | G | g | A | _a_ | _A_ | _A_ | c | _T_ | g | _G_ | _A_ | 12 |
| 11239 | | T | c | _C_ | _T_ | G | G | g | A | _a_ | _A_ | _a_ | c | _T_ | g | g | _A_ | 13 |
| 11241 | | T | c | _C_ | t | G | g | G | a | _A_ | _a_ | _A_ | c | _T_ | g | _G_ | _A_ | 14 |
| 11242 | | T | c | c | _T_ | G | g | G | a | _A_ | _A_ | _a_ | _C_ | _t_ | _G_ | g | _A_ | 15 |
| 11244 | | T | c | _C_ | _T_ | g | g | G | A | _a_ | _A_ | _a_ | _C_ | _t_ | _G_ | g | _A_ | 16 |
| 11318 | | T | c | c | t | G | G | g | a | _A_ | _A_ | _A_ | c | _T_ | g | _G_ | _A_ | 17 |
| 11319 | | T | _C_ | c | t | g | G | g | A | _a_ | _A_ | _A_ | c | _T_ | g | _G_ | _A_ | 18 |
| 11320 | | T | _C_ | c | t | g | G | G | a | _a_ | _A_ | _A_ | _C_ | _t_ | _G_ | g | _A_ | 19 |
| 11321 | | T | c | c | t | G | G | g | A | _a_ | _A_ | _A_ | c | _T_ | g | _G_ | _A_ | 20 |

TABLE 2

Description of Notations

| | |
|---|---|
| deoxy A | a |
| deoxy G | g |
| deoxy C | c |
| deoxy T | t |
| lna A | A |
| lnaG | G |
| lna C | C |
| lna T | T |

Figure 3:
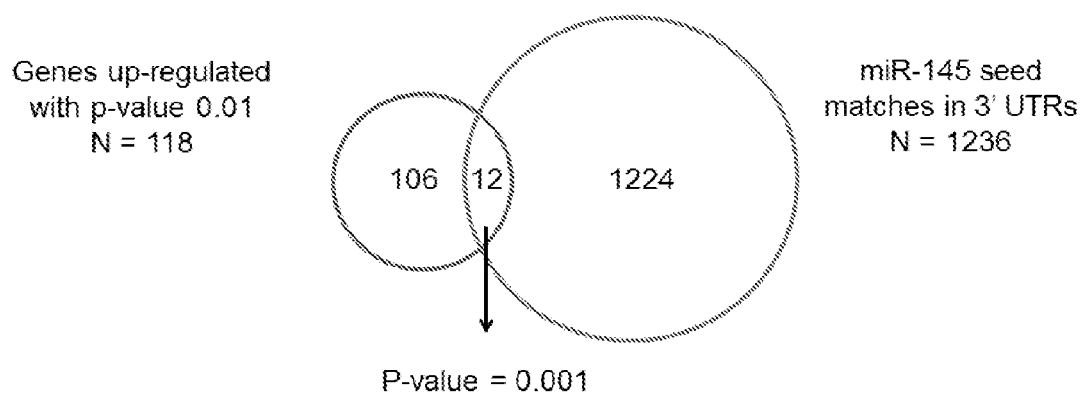
FIG. 3. M-11318-treated lung total RNA and saline-treated lung total RNA were subjected to whole genome profiling with microarray profiling. MiR-145 seed-containing genes are enriched in the upregulated gene signature (p-value <0.01 for differential expression) when M-11318-treated lung total RNA is compared to saline-treated total RNA. The p-value for enrichment was calculated using a hypergeometric distribution function. This result indicates M-11318 elicits gene target derepression that is specific to miR-145.

The nine antimiR compounds in Table 1 were assayed for target derepression in the Sprague-Dawley rats. Sprague-Dawley rats of 49 to 52 days of age were injected subcutaneously at a dose of 25 mg/kg of an antimiR compound from Table 1. Saline and an oligonucleotide with similar LNA and DNA percentage (9/7) were used as controls. The oligonucleotide control, molecule number M-10591, was designed to target a *C. elegans*-specific miRNA and used as mg/kg. Total RNA from the lungs of M-11318-treated rats and saline-treated rats were subjected to whole genome profiling with microarray profiling. MiR-145 seed-containing genes are enriched in the upregulated gene signature (p-value <0.01 for differential expression) when total RNA from the lungs of M-11318-treated rats is compared to total RNA from the lungs of saline-treated rats. The p-value for enrichment was calculated using a hypergeometric distribution function (FIG. 3). These results indicate that M-11318 elicits gene target derepression that is specific to miR-145.

Example 3. Dose-Dependent Target Derepression by AntimiR-145 Compound M-11318

Figure 4:
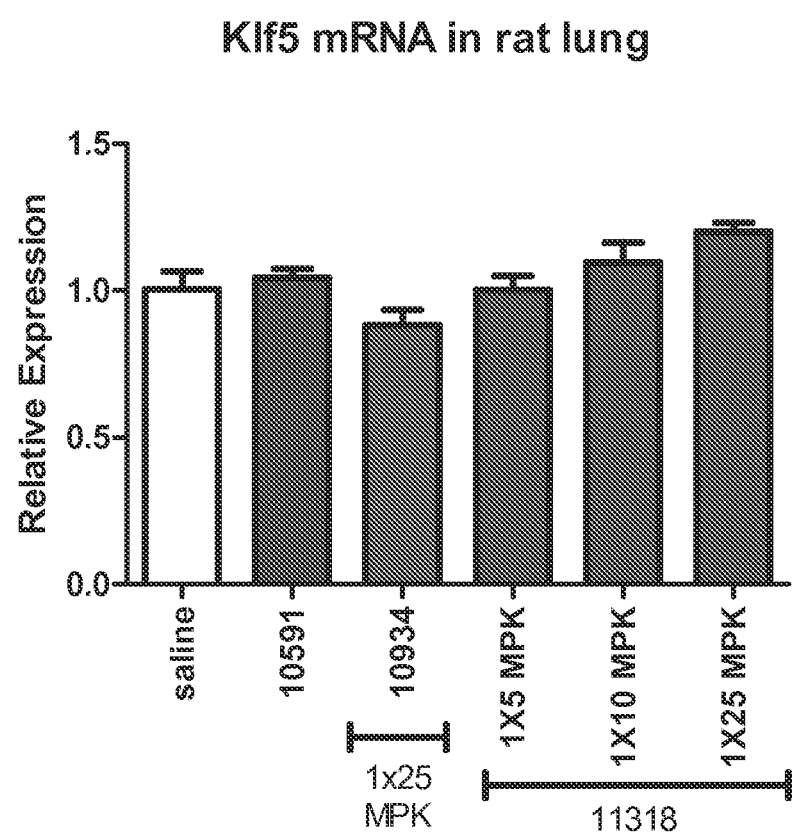
FIG. 4. Sprague-Dawley rats of 49 to 52 days of age were injected with a 5, 10, or 25 mg/kg subcutaneous dose of M-11318. Tissue was collected 48 hours after injection. The indicated mRNAs were measured by real time PCR in total lung RNA. The results are shown as fold-change values relative to saline-treated animals. The real time PCR results suggest that KLF5 target derepression is dose-responsive to M-11318 treatment.

Sprague-Dawley rats of 49 to 52 days of age were injected subcutaneously with saline at a dose of 25 mg/kg, M-10591 at a dose of 25 mg/kg, M-10934 at a dose of 25 mg/kg, or M-11318 at a dose of 5 mg/kg, 10 mg/kg, or 25 mg/kg. Lung tissue was collected 72 hours after injection. The mRNA of Klf5 in total lung RNA was measured by real time PCR. The results are shown in FIG. 4 as fold-change values relative to saline-treated animals. The real time PCR results indicates that KLF5 target derepression is dose-responsive to M-11318 treatment.

Example 4. Dose-Dependent Target Derepression by AntimiR-145 Compounds M-11318 and M-11319

Figure 5:
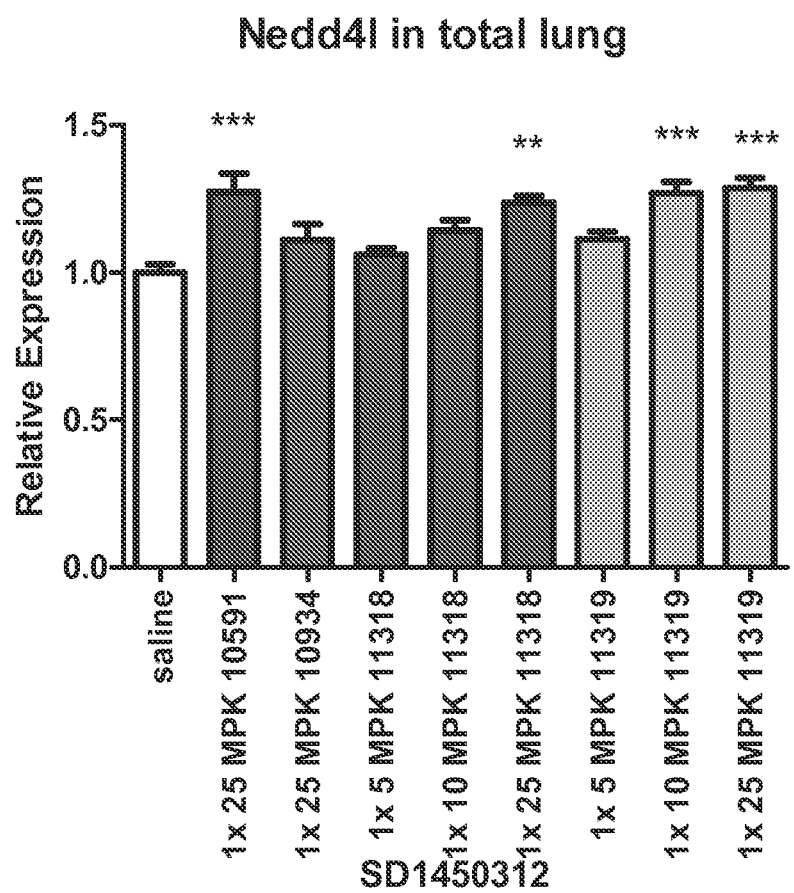
FIG. 5. Sprague-Dawley rats of 49 to 52 days of age were injected with a 5, 10, or 25 mg/kg subcutaneous dose of M-11318 or M-11319. Tissue was collected 48 hours after injection. The indicated mRNAs were measured by real time PCR in total lung RNA. The results are shown as fold-change values relative to saline-treated animals. The real time PCR results suggest that Nedd41 target derepression is dose-responsive to M-11318 and M-11319 treatment.

Sprague-Dawley rats of 49 to 52 days of age were injected subcutaneously with saline at a dose of 25 mg/kg, M-10591 at a dose of 25 mg/kg; M-10934 at a dose of 25 mg/kg; M-11318 at a dose of 5 mg/kg, 10 mg/kg, or 25 mg/kg; or M-11319 at a dose of 5 mg/kg, 10 mg/kg, or 25 mg/kg. Lung tissue was collected 48 hours after injection. The mRNA of Nedd41 in total lung RNA was measured by real time PCR. The results are shown in FIG. 5 as fold-change values relative to saline-treated animals. The real time PCR results indicate that Nedd41 target derepression is dose-responsive to M-11318 and M-11319 treatment.

Example 5. AntimiR-145 Reduced Systemic Blood Pressure and Indices of Arterial Stiffening Spontaneously Hypertensive (SHR) rats at 16 weeks of age were subjected to four weekly 25 mg/kg subcutaneous doses of antimiR. At 18 weeks, L-NG-Nitroarginine Methyl Ester (L-NAME) was administered in the drinking water (50 mg/L), given ad libitum for 2 weeks to create a therapeutic window in pulse-wave velocity (PWV) measurements. At study's end, when the rats are at 20 weeks of age, terminal pulse-wave velocity, beta index, and blood pressure were measured. (FIG. 6A) Perindopril, an ACE inhibitor, was included in the study as a benchmark for one standard of care for hypertension.

Figures 6B, 6C:
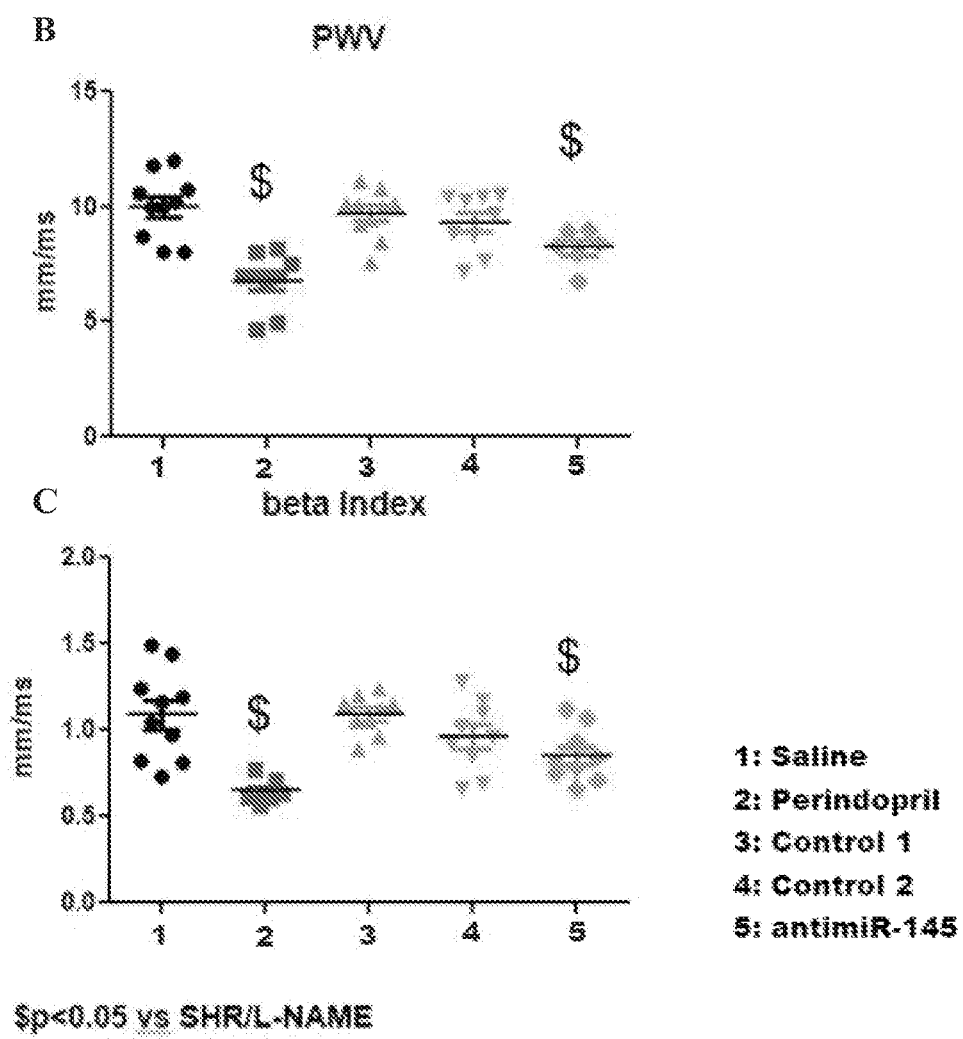
FIG. 6. (A) Spontaneously Hypertensive (SHR) rats at 16 weeks of age were subjected to four weekly 25 mg/kg subcutaneous doses of antimiR. At 18 weeks, L-NG-Nitroarginine Methyl Ester (L-NAME) was administered in the drinking water (50 mg/L), given ad libitum for 2 weeks to create a therapeutic window in pulse-wave velocity (PWV) measurements. At study's end, when the rats are at 20 weeks of age, terminal pulse-wave velocity, beta index, and blood pressure were measured. Perindopril, an ACE inhibitor, was included in the study as a benchmark for one standard of care for hypertension. AntimiR-145 (M-10934) showed a statistically-significant reduction in pulse-wave velocity (B), beta index (C), and mean system pressure (D). Importantly, two other control antimiRs (Control 1 and Control 2) did not show a similar benefit with this dose and regime, thereby showing the microRNA specificity of this therapeutic effect. (B-D). Together, these results demonstrated that miR-145 inhibition has therapeutic benefit in the rat SHR/L-NAME of hypertension. AntimiR-145 reduced systemic blood pressure and indices of arterial stiffening.
Figure 6D:
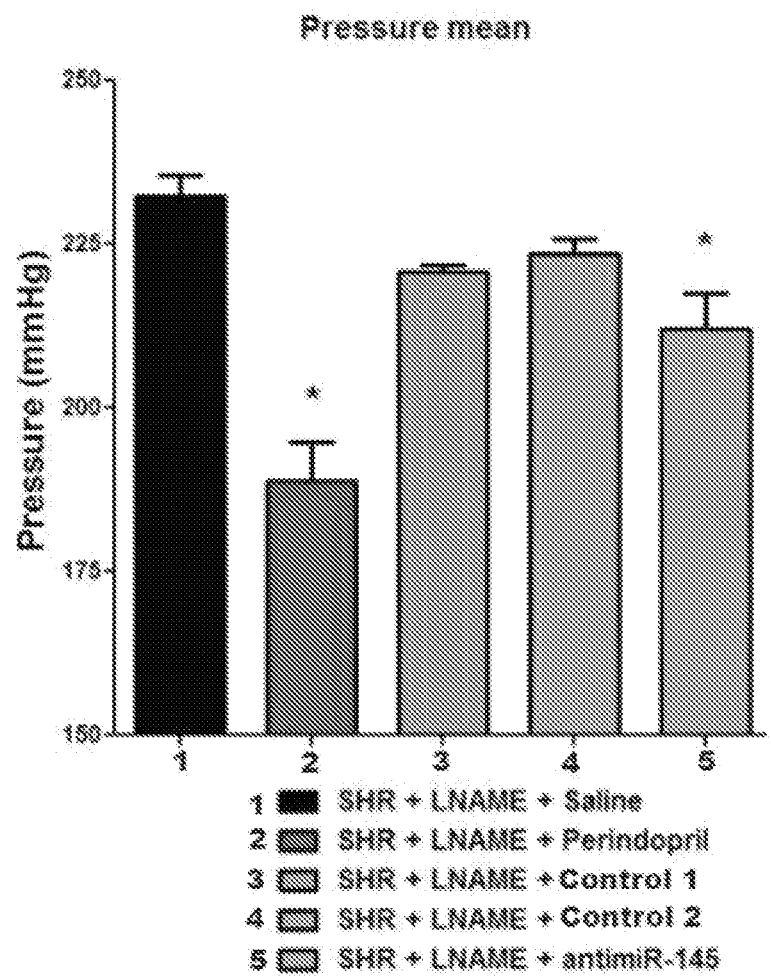

AntimiR-145 (M-10934) showed a statistically-significant reduction in pulse-wave velocity (FIG. 6B), beta index (FIG. 6C), and mean system pressure (FIG. 6D). Importantly, two other control antimiRs (Control 1 and Control 2) did not show a similar benefit with this dose and regime, thereby showing the microRNA specificity of this therapeutic effect. (FIG. 6B-6D). Together, these results demonstrated that miR-145 inhibition has therapeutic benefit in the rat SHR/L-NAME of hypertension.

All publications, patents, and patent applications discussed and cited herein are incorporated herein by reference in their entireties. It is understood that the disclosed invention is not limited to the particular methodology, protocols and materials described as these can vary. It is also understood that the terminology used herein is for the purposes of describing particular embodiments only and is not intended to limit the scope of the present invention which will be limited only by the appended claims.

Those skilled in the art will recognize, or be able to ascertain using no more than routine experimentation, many equivalents to the specific embodiments of the invention described herein. Such equivalents are intended to be encompassed by the following claims.

REFERENCES

1. Mandegar M, Fung Y C, Huang W, Remillard C V, Rubin L J, Yuan J X. Cellular and molecular mechanisms of pulmonary vascular remodeling: Role in the development of pulmonary hypertension. Microvasc Res. 2004; 68:75-103
2. Ambros V. The functions of animal micrornas. Nature. 2004; 431:350-355
3. Bartel D P. Micrornas: Target recognition and regulatory functions. Cell. 2009; 136:215-233
4. Guo H, Ingolia N T, Weissman J S, Bartel D P. Mammalian micrornas predominantly act to decrease target mrna levels. Nature. 2010; 466:835-840
5. Kartha R V, Subramanian S. Micrornas in cardiovascular diseases: Biology and potential clinical applications. J Cardiovasc Transl Res. 2010; 3:256-270
6. Urbich C, Kuehbacher A, Dimmeler S. Role of micrornas in vascular diseases, inflammation, and angiogenesis. Cardiovasc Res. 2008; 79:581-588
7. Cheng Y. Liu X, Yang J, Lin Y, Xu D Z, Lu Q, Deitch E A, Huo Y, Delphin E S, Zhang C. Microrna-145, a novel smooth muscle cell phenotypic marker and modulator, controls vascular neointimal lesion formation. Circ Res. 2009; 105:158-166
8. Lio A, Nakagawa Y. Hirata I, Naoe T, Akao Y. Identification of non-coding RNAs embracing microrna-143/145 cluster. Mol Cancer. 2010; 9:136
9. Xin M, Small E M, Sutherland L B. Qi X. McAnally J, Plato C F, Richardson J A, Bassel-Duby R, Olson E N. Micrornas mir-143 and mir-145 modulate cytoskeletal dynamics and responsiveness of smooth muscle cells to injury. Genes Dev. 2009; 23:2166-2178
10. Elia L, Quintavalle M, Zhang J, Contu R, Cossu L, Latronico M V, Peterson K L, Indolfi C, Catalucci D, Chen J, Courtneidge S A, Condorelli G. The knockout of mir-143 and -145 alters smooth muscle cell maintenance and vascular homeostasis in mice: Correlates with human disease. Cell Death Differ. 2009; 16:1590-1598
11. Davis-Dusenbery B N, Chan M C, Reno K E, Weisman A S, Layne M D, Lagna G, Hata A. Downregulation of klf4 by mir-143/145 is critical for modulation of vascular smooth muscle cell phenotype by tgf-{beta} and bmp. J Biol Chem. 2011; 286:28097-110
12. Long X, Miano J M. Tgf{beta}1 utilizes distinct pathways for the transcriptional activation of microrna 143/145 in human coronary artery smooth muscle cells. J Biol Chem. 2011; 286, 30119-30129

The invention claimed is:

1. An oligonucleotide comprising a sequence complementary to the seed region of miR-145, wherein the seed region is 5'-UCCAGUUU-3' (SEQ ID NO: 7), wherein the oligonucleotide consists of sixteen nucleotides, wherein from the 5' end to the 3' end, the oligonucleotide comprises LNAs at positions 1, 6, 11, 13 and 15 of the sequence, and wherein the oligonucleotide comprises at least one non-locked nucleotide.

2. The oligonucleotide of claim 1, wherein the oligonucleotide comprises a LNA at a 5' end, a 3' end or both a 5' and a 3' end.

3. The oligonucleotide of claim 1, wherein the oligonucleotide comprises no more than three contiguous LNAs.

4. The oligonucleotide of claim 1, wherein the oligonucleotide comprises at least nine LNAs.

5. The oligonucleotide of claim 4, wherein from the 5'end to the 3' end of the oligonucleotide, positions 5, 9, 10 and 16 are LNAs.

6. The oligonucleotide of claim 4, wherein from the 5'end to the 3' end of the oligonucleotide, positions 2, 8, 10 and 16 are LNAs.

7. The oligonucleotide of claim 1, wherein at least one of the non-locked nucleotides is 2' deoxy, 2' O-alkyl or 2' halo.

8. The oligonucleotide of claim 1, wherein the oligonucleotide has a 5' cap structure, 3' cap structure, or 5' and 3' cap structure.

9. The oligonucleotide of claim 1, wherein the oligonucleotide comprises one or more phosphorothioate linkages.

10. The oligonucleotide of claim 1, wherein the oligonucleotide has one to three phosphate linkages.

11. The oligonucleotide of claim 1, further comprising a pendant lipophilic group.

12. The oligonucleotide of claim 1, wherein the oligonucleotide increases the expression of a miR-145 target gene in a cell relative to a saline control, and the increase in expression has a p-value of <0.05.

13. The oligonucleotide of claim 12, wherein the miR-145 target gene is Klf4, Klf5, Lrrc71, Nedd4l, Igf1r, Sec14l2, Megf6, Fmod, Ankrd12, Golga1, Gpbp1, Hist3h2a, Rapgef2, or Sned1.

14. A method of reducing or inhibiting activity of miR-145 in a cell comprising contacting the cell with the oligonucleotide of claim 1.

15. A method of inhibiting smooth muscle cell proliferation comprising contacting a smooth muscle cell with the oligonucleotide of claim 1.

16. A method of inhibiting or treating restenosis or neointima formation in a subject comprising administering to the subject a pharmaceutical composition comprising the oligonucleotide of claim 1.

17. A method of treating or preventing hypertension in a subject comprising administering to the subject a pharmaceutical composition comprising the oligonucleotide of claim 1.

18. The oligonucleotide of claim 1, wherein the oligonucleotide has increased in vivo efficacy as compared to a second oligonucleotide comprising the same sequence and LNA composition and different LNA motif.

19. The oligonucleotide of claim 18, wherein the oligonucleotide has increased lung efficacy as compared to the second oligonucleotide.

* * * * *